US012664368B2

(12) United States Patent
Odland et al.

(10) Patent No.: US 12,664,368 B2
(45) Date of Patent: Jun. 23, 2026

(54) DYNAMICALLY GENERATED LLM REQUEST PACKAGE TO GENERATE A HUMAN-READABLE RESPONSE COMPRISING SENSITIVE DATA TO A USER INPUT

(71) Applicant: PLAYBACK HEALTH INC., Brooklyn, NY (US)

(72) Inventors: Gregory Odland, Brooklyn, NY (US); Simerjot Singh, New Hyde Park, NY (US)

(73) Assignee: PLAYBACK HEALTH INC., Brooklyn, NY (US)

( * ) Notice: Subject to any disclaimer, the term of this patent is extended or adjusted under 35 U.S.C. 154(b) by 80 days.

(21) Appl. No.: 18/752,396

(22) Filed: Jun. 24, 2024

(65) Prior Publication Data

US 2024/0427994 A1     Dec. 26, 2024

Related U.S. Application Data

(60) Provisional application No. 63/510,012, filed on Jun. 23, 2023.

(51) Int. Cl.
*G06F 21/62*          (2013.01)
*G06F 40/284*          (2020.01)
(Continued)

(52) U.S. Cl.
CPC ........ *G06F 40/284* (2020.01); *G06F 21/6245* (2013.01); *G16H 10/60* (2018.01); *G16H 50/20* (2018.01)

(58) Field of Classification Search
CPC ............................... G16H 10/60; G16H 50/20
See application file for complete search history.

(56) References Cited

U.S. PATENT DOCUMENTS 11,531,846 B1    12/2022  Bodapati et al.
2017/0235971 A1*  8/2017  Kline ..................... G16H 10/60
                                                    713/193

(Continued)

FOREIGN PATENT DOCUMENTS

CN          114999676 A      9/2022
CN          116738476 A      9/2023

(Continued)

OTHER PUBLICATIONS

Compliancy Group, AI Rising: ChatGPT, Healthcare, and HIPAA Compliance, Jan. 27, 2023, accessed Apr. 12, 2023, www.compliancy-group.com/hipaa-and-chatgpt/.

(Continued)

*Primary Examiner* — Farzad Kazeminezhad
(74) *Attorney, Agent, or Firm* — Definitive Patents, member Synchrony IP; Timothy D. Snowden; Yau H. Chan

(57)          ABSTRACT

Apparatus and associated methods relate to automatically generating secured artificial intelligence input packages from sensitive data input. In an illustrative example, a sensitive questions answering system (SQAS) may receive a natural language input (NLI). For example, the SQAS may retrieve sensitive data related to the NLI. In some implementations, the SQAS may be configured to desensitize the sensitive data and/or generate a secured user input and media objects to be combined into a secured LLM (large language model) input array. For example, the secured LLM input array may be provided to an unsecured LLM to generate a human-readable response (HRR). In some implementations, a sensitized response may be generated by reintroducing some of the sensitive data to the HRR. For example, the sensitized response may include personal data. Various embodiments may advantageously ensure the secure (Continued)

handling of sensitive data while providing personal responses to user queries.

20 Claims, 20 Drawing Sheets

(51) Int. Cl.
   *G16H 10/60*          (2018.01)
   *G16H 50/20*          (2018.01)

(56)                    References Cited

U.S. PATENT DOCUMENTS

| | | |
|---|---|---|
| 2020/0211709 A1 | 7/2020 | Devesa |
| 2022/0399086 A1 | 12/2022 | Simons et al. |
| 2024/0095455 A1 | 3/2024 | Sharma et al. |
| 2024/0104336 A1 | 3/2024 | Irving et al. |

FOREIGN PATENT DOCUMENTS

| | | |
|---|---|---|
| CN | 116861480 A | 10/2023 |
| CN | 117493483 A | 2/2024 |
| CN | 117633166 A | 3/2024 |
| CN | 117708301 A | 3/2024 |
| CN | 117725610 A | 3/2024 |
| CN | 117851558 A | 4/2024 |

OTHER PUBLICATIONS

Levitt, D, A quick guide to using ChatGPT in a HIPAA compliant way, Mar. 28, 2023, accessed Apr. 12, 2023, www.paubox.com/blog/a-quick-guide-to-using-chatgpt-in-a-hipaa-compliant-way.

Turner, B, Epic, Microsoft bring GPT-4 to EHRs, Modern Health-care, Apr. 17, 2023, accessed Apr. 21, 2023, www.modernhealthcare.com/digital-health/himss-2023-epic-microsoft-bring-openais-gpt-4-ehrs.

Turner, B, Microsoft, Nuance bring ChatGPT successor to health-care, Digital Health, Mar. 20, 2023, accessed Apr. 21, 2023, www.digitalhealth.modernhealthcare.com/digital-health/nuance-microsoft-chatgpt-gpt4-EHR.

* cited by examiner

400

405
Training
Input Data

415
Evaluation
Vectors

420
User
Engagement

245
Machine Learning Engine

410
Training
Output Data

425
Training Vectors

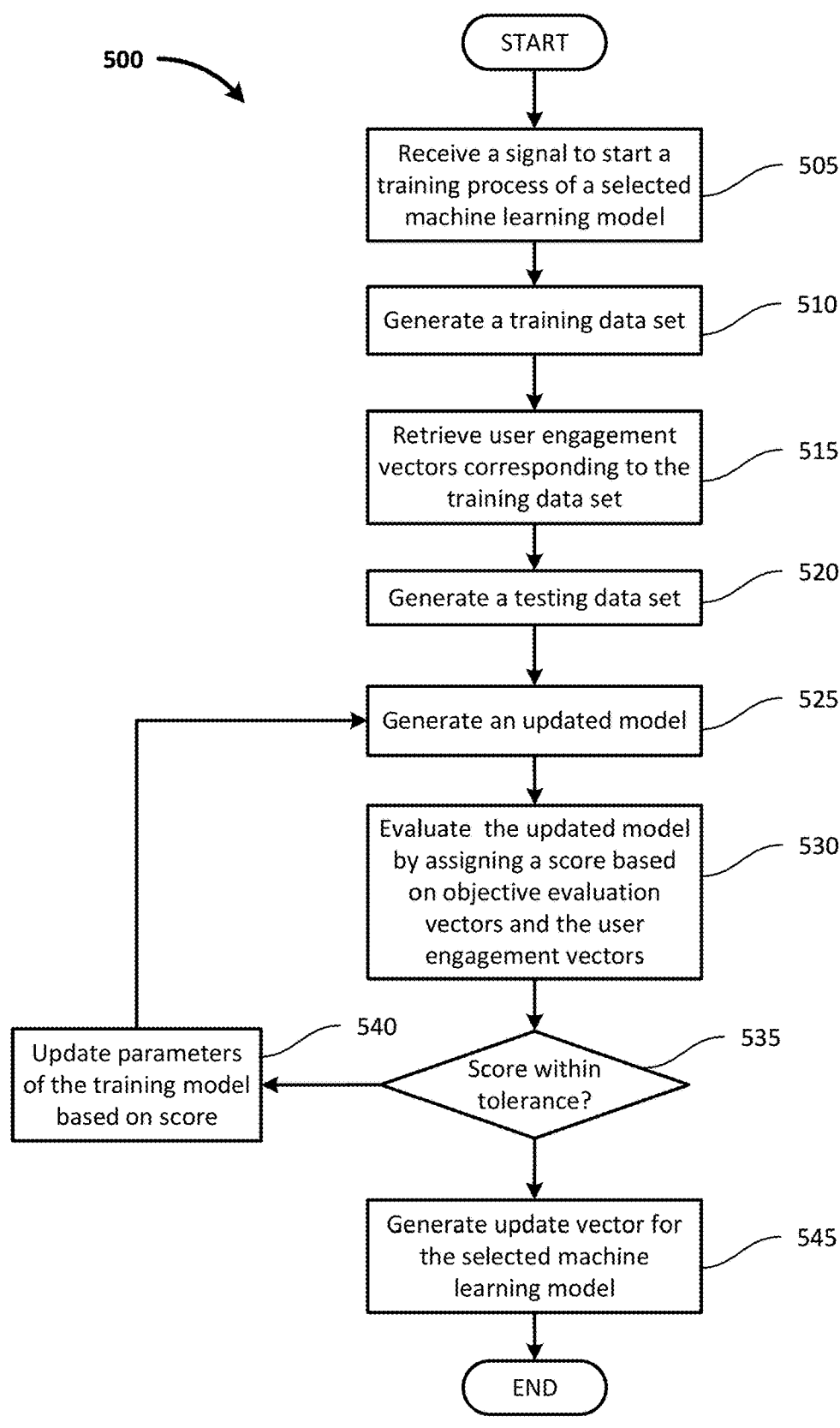

500

START

Receive a signal to start a training process of a selected machine learning model — 505

Generate a training data set — 510

Retrieve user engagement vectors corresponding to the training data set — 515

Generate a testing data set — 520

Generate an updated model — 525

Evaluate the updated model by assigning a score based on objective evaluation vectors and the user engagement vectors — 530

Update parameters of the training model based on score — 540

Score within tolerance? — 535

Generate update vector for the selected machine learning model — 545

END

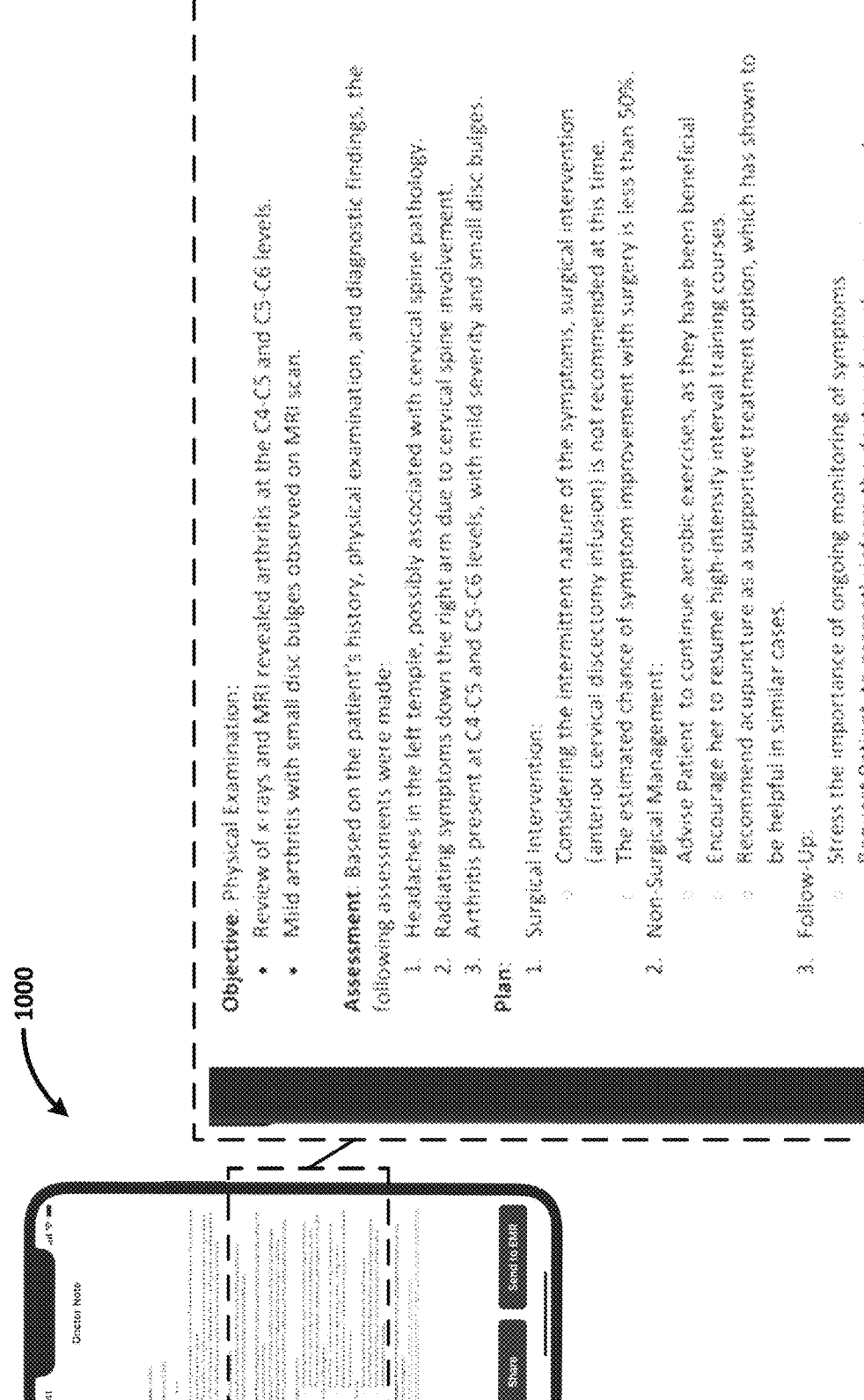

Objective: Physical Examination:
* Review of x-rays and MRI revealed arthritis at the C4-C5 and C5-C6 levels.
* Mild arthritis with small disc bulges observed on MRI scan.

Assessment: Based on the patient's history, physical examination, and diagnostic findings, the following assessments were made:
1. Headaches in the left temple, possibly associated with cervical spine pathology.
2. Radiating symptoms down the right arm due to cervical spine involvement.
3. Arthritis present at C4-C5 and C5-C6 levels, with mild severity and small disc bulges.

Plan:
1. Surgical Intervention:
   ○ Considering the intermittent nature of the symptoms, surgical intervention (anterior cervical discectomy infusion) is not recommended at this time.
   ○ The estimated chance of symptom improvement with surgery is less than 50%.
2. Non-Surgical Management:
   ○ Advise Patient to continue aerobic exercises, as they have been beneficial.
   ○ Encourage her to resume high-intensity interval training courses.
   ○ Recommend acupuncture as a supportive treatment option, which has shown to be helpful in similar cases.
3. Follow-Up:
   ○ Stress the importance of ongoing monitoring of symptoms.
   ○ Request Patient to promptly inform the doctor of any changes in symptoms.
   ○ Arrange for regular follow-up visits to assess progress and make further recommendations as needed.

FIG. 10B

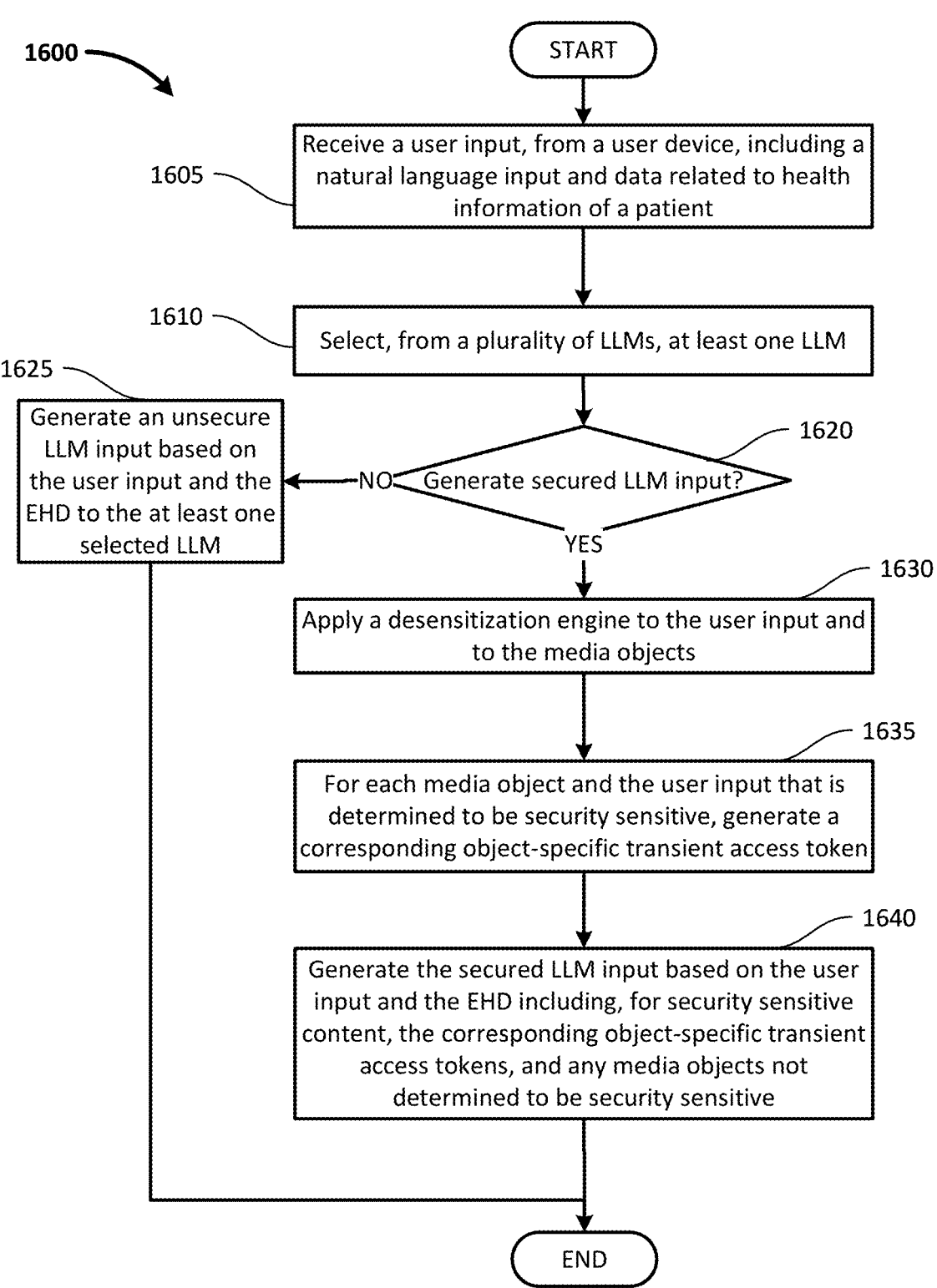

1600

START

1605 — Receive a user input, from a user device, including a natural language input and data related to health information of a patient 1610 — Select, from a plurality of LLMs, at least one LLM 1620 — Generate secured LLM input?

1625 — Generate an unsecure LLM input based on the user input and the EHD to the at least one selected LLM

NO

YES

1630 — Apply a desensitization engine to the user input and to the media objects 1635 — For each media object and the user input that is determined to be security sensitive, generate a corresponding object-specific transient access token 1640 — Generate the secured LLM input based on the user input and the EHD including, for security sensitive content, the corresponding object-specific transient access tokens, and any media objects not determined to be security sensitive

END

DYNAMICALLY GENERATED LLM REQUEST PACKAGE TO GENERATE A HUMAN-READABLE RESPONSE COMPRISING SENSITIVE DATA TO A USER INPUT

CROSS-REFERENCE TO RELATED APPLICATIONS

This application also claims the benefit of U.S. Provisional Application Ser. No. 63/510,012, titled "DYNAMICALLY GENERATED LARGE LANGUAGE MODEL HEALTH REQUEST PACKAGE," filed by Gregory Odland, et al., on Jun. 23, 2023.

This application incorporates the entire contents of the foregoing application(s) herein by reference.

The subject matter of this application may have common inventorship with and/or may be related to the subject matter of the following:

PCT Patent Application Serial No. PCT/US22/72888, titled "MULTI-PARTY CONTROLLED TRANSIENT USER CREDENTIALING FOR INTERACTION WITH PATIENT HEALTH DATA," filed by Gregory Odland, et al., on Jun. 10, 2022;

U.S. application Ser. No. 17/806,446, titled "MULTI-PARTY CONTROLLED TRANSIENT USER CREDENTIALING FOR INTERACTION WITH PATIENT HEALTH DATA," filed by Gregory Odland, et al., on Jun. 10, 2022;

U.S. application Ser. No. 16/876,083, titled "APPARATUS FOR GENERATING AND TRANSMITTING ANNOTATED VIDEO SEQUENCES IN RESPONSE TO MANUAL AND IMAGE INPUT DEVICES," filed by Gregory Odland, et al., on May 17, 2020.

U.S. Application Ser. No. 62/849,716, titled "PATIENT COMMUNICATION AND NOTIFICATION SYSTEM WITH PROVIDER AND PATIENT MULTIPLY SOURCED AND UPDATED DATABASES AND INFORMATION COMMUNICATIONS BACKBONE," filed by David Langer, et al., on May 17, 2019;

U.S. Application Ser. No. 62/947,544, titled "HEALTHCARE PROVIDER AND PATIENT COMMUNICATIONS SYSTEM," filed by David Langer, et al., on Dec. 13, 2019;

U.S. application Ser. No. 16/876,083, titled "APPARATUS FOR GENERATING AND TRANSMITTING ANNOTATED VIDEO SEQUENCES IN RESPONSE TO MANUAL AND IMAGE INPUT DEVICES," filed by David Langer, et al., on May 17, 2020; and, PCT Application Serial No. PCT/US2020/033328, titled "APPARATUS FOR GENERATING AND TRANSMITTING ANNOTATED VIDEO SEQUENCES IN RESPONSE TO MANUAL AND IMAGE INPUT DEVICES," filed by David Langer, et al., on May 17, 2020.

This application incorporates the entire contents of the foregoing application(s) herein by reference.

TECHNICAL FIELD

Various embodiments relate generally to generative health inquiry and response systems.

BACKGROUND

Large language models (LLMs) may recently have become increasingly popular as a tool for generating human-like responses to various prompts. For example, some models, such as third-generation Generative Pre-trained Transformer (GPT-3), may be trained on vast amounts of text data and can be used to perform a wide range of tasks, from language translation to text generation.

For example, one widely used application of these models may be in chatbots. For example, a chatbot may use the language model's capabilities to communicate with users in a conversational manner. Some chatbots may have become an increasingly common feature on websites and mobile apps, for example. These chatbots, for example, may allow a business to provide 24/7 customer support and assistance without requiring human operators.

In e-commerce, chatbots may have been used to great effect in assisting customers with their purchases. Some chatbots may, for example, provide personalized recommendations and answer specific questions about products and services. Sometimes, applications of chatbots may increase customer satisfaction and loyalty, reduce clinical time required to answer consumer questions, and generate higher sales and revenue for businesses.

SUMMARY

Apparatus and associated methods relate to automatically generating secured artificial intelligence input packages from sensitive data input. In an illustrative example, a sensitive questions answering system (SQAS) may receive a natural language input (NLI). For example, the SQAS may retrieve sensitive data related to the NLI. In some implementations, the SQAS may be configured to desensitize the sensitive data and/or generate a secured user input and media objects to be combined into a secured LLM (large language model) input array. For example, the secured LLM input array may be provided to an unsecured LLM to generate a human-readable response (HRR). In some implementations, a sensitized response may be generated by reintroducing some of the sensitive data to the HRR. For example, the sensitized response may include personal data. Various embodiments may advantageously ensure the secure handling of sensitive data while providing personal responses to user queries.

Apparatus and associated methods relate to securely transmitting artificial intelligence input packages with sensitive data. In an illustrative example, a SQAS may generate a secured large language model (LLM) input array based on user input and electronic health data (EHD) of a patient. The SQAS may determine, for example, an appropriate LLM from multiple LLMs. Sensitive data within the user input and media objects may, for example, be processed by a desensitization engine, generating object-specific transient access tokens (OSTAT) for security-sensitive data. In some implementations, the secured LLM input array may include one or more OSTATs and non-sensitive media objects. For example, the selected LLM may gain a transient availability of security-sensitive media objects via the access tokens for generating a human-readable response. Various embodiments may advantageously ensure secure transmission and processing of sensitive data while providing accurate and protected responses to user queries.

Apparatus and associated methods relate to a medical records interaction system (MRIS). In an illustrative example, the MRIS may dynamically generate a de-identified (e.g., HIPPA-compliant) sensitive records package for delivery to a LLM to answer a question from a user. The user, for example, may ask a question related to a medical record (e.g., a post-surgery care instruction). For example, the MRIS may generate a question answer package (QAP) for transmitting to one or more external LLMs with the user's question. For example, the QAP may be generated based on the user's questions and the user's sensitive medical record. The QAP may be sanitized to remove any personally identifying data. Various embodiments may advantageously allow a non-private LLM to provide dynamic answers to patient questions using the patient's own medical records by dynamically deidentifying the data before providing it to the LLM.

Various embodiments may achieve one or more advantages. For example, some embodiments may advantageously enable the use of publicly available LLMs trained on vast amounts of data, while still handling sensitive customer information carefully and in compliance with relevant data privacy laws. For example, some embodiments may advantageously provide a technical solution to a problem of when and/or how to use publicly available models (e.g., LLMs, natural language query (NLQ), other artificial intelligence models) to answer questions using sensitive data unwise, unethical, and/or prohibited (e.g., by law, by contract) to provide to a publicly available model. Some embodiments may, for example, advantageously retrieve the user's medical content including structured data such as lab results, diagnostic images, discharge records, and/or unstructured data such as video, audio, documents, and/or other media messages. Some embodiments, for example, may advantageously transcribe audio and/or video medical content to remove personally identifying data from the transcription. For example, some embodiments may advantageously select a LLM to deliver the QAP based on historical answers/ results. Some embodiments, for example, may advantageously allow a non-private LLM to provide dynamic answers to patient questions using the patient's own medical records by dynamically deidentifying the data before providing it to the LLM. For example, some embodiments may advantageously generate answers based on a user's identity (e.g., patient, caretaker of a patient, medical professional related to the patient). Some embodiments, for example, may dynamically source the patient data as a function of the requestor's role, the requestor's access permission, and/or a content creator's permissions. For example, some embodiments may advantageously infer a question context and dynamically select content to be included in an answer.

The details of various embodiments are set forth in the accompanying drawings and the description below. Other features and advantages will be apparent from the description and drawings, and from the claims.

BRIEF DESCRIPTION OF THE DRAWINGS

FIG. 5 depicts an exemplary method of training a content characterization engine.

FIG. 8 is a flowchart illustrating an exemplary query answer package (QAP) routing method.

FIG. 10A, FIG. 10B, and FIG. 10C depict an exemplary doctor note displayed on a user device.

FIG. 16 is a flowchart illustrating an exemplary tokenized sensitive inquiry routing method.

Like reference symbols in the various drawings indicate like elements.

DETAILED DESCRIPTION OF ILLUSTRATIVE EMBODIMENTS

To aid understanding, this document is organized as follows. First, to help introduce discussion of various embodiments, a medical records interaction system (MRIS) is introduced with reference to FIGS. 1-2. Second, that introduction leads into a description with reference to FIGS. 3-4 of some exemplary embodiments of a health information generative system (HIGS). Third, with reference to FIGS. 5-8, this document describes exemplary apparatus and methods useful for generating accurate and relatable answers to user's questions while complying with relevant privacy rules. Fourth, with reference to FIGS. 9-14, the discussion turns to exemplary embodiments that illustrate exemplary user interfaces for using the HIGS. Fifth, and with reference to FIGS. 15-17, this document describes exemplary apparatus and methods useful for securely transmitting artificial intelligence input packages with sensitive data. Finally, the document discusses further embodiments, exemplary applications and aspects relating to the HIGS.

Figure 1:
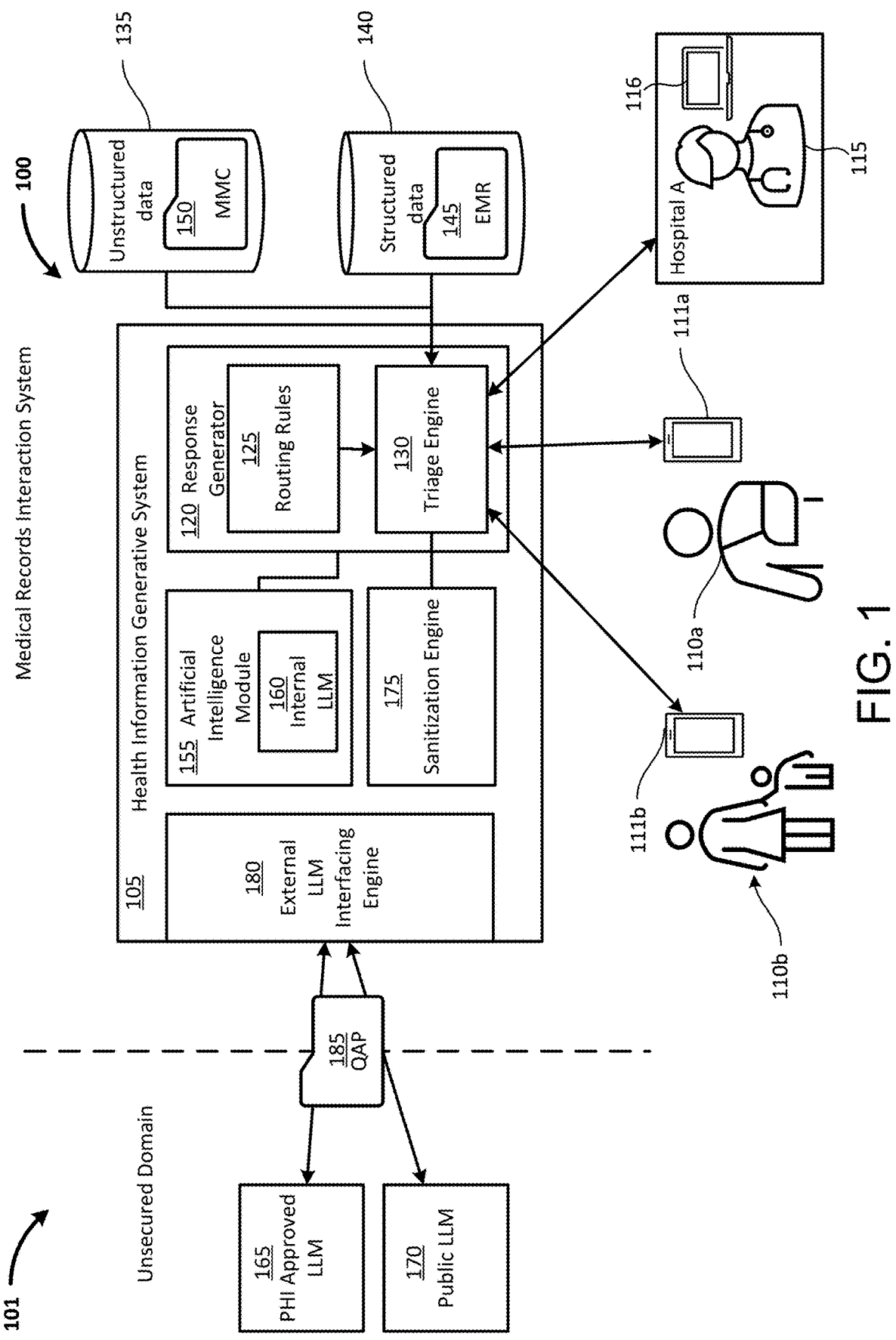
FIG. 1 depicts an exemplary medical records interaction system (MRIS) employed in an illustrative use-case scenario.

FIG. 1 depicts an exemplary medical records interaction system (MRIS 100) employed in an illustrative use-case scenario. For example, the MRIS 100 may dynamically generate a desensitized query package (e.g., HIPPA-compliant) for delivery to a LLM to answer a question from a user. In this example, the MRIS 100 includes a health information generative system (HIGS 105). The HIGS 105, for example, may selectively gather various content to answer questions from users.

As shown, the HIGS 105 receives queries from a patient 110a and a user 110b. For example, the patient 110a may be a patient who just received a medical treatment for his broken arm. For example, the user 110b may be a family member of the patient 110a. In this example, the patient 110a may use a mobile device 111a to transmit a question to the HIGS 105. For example, the patient 110a may ask a question related to his private medical record (e.g., "what medication should I be taking?", "what is my after discharge care?"). The user 110b may use a mobile device 111b to transmit a question about a timing of future medical appointments for the patient 110a. For example, the mobile device 111a and the mobile device 111b may include a dedicated application to communicate with the HIGS 105. In some examples, the mobile device 111a and/or the mobile device 111b may communicate with the HIGS 105 via a web interface (e.g., using a web browser).

The HIGS 105 may also receive questions from a medical professional 115 (e.g., a caretaker, a physician, etc.). For example, the medical professional 115 may generate an inquiry using a computing device 116 about a specific status of the patient 110a. For example, the medical professional 115 may request a schedule of future appointment dates of the patient 110a. In some examples, the medical professional 115 may be newly assigned to care of the patient 110a. For example, the medical professional 115 may request to review previous care instructions sent to the patient 110a before an appointment.

In some implementations, the HIGS 105 may generate an answer to the patient 110a or the user 110b based on permissions, token, scope of a question, type of a question, or a combination thereof. For example, the HIGS 105 may generate a filtered answer to the user 110b to remove sensitive data not applicable to the user 110b. Various embodiments of providing permissions and/or time-limited tokens for a user to review electronic medical content are described in U.S. application Ser. No. 17/806,446, titled "Multi-party Controlled Transient User Credentialing for Interaction with Patient Health Data," filed by Gregory Odland, et al., on Jun. 10, 2022. This application incorporates the entire contents of the foregoing application herein by reference.

The HIGS 105 includes a response generator 120. In this example, the response generator 120 includes routing rules 125 and a triage engine 130. For example, the triage engine 130 may receive questions from the patient 110a, the user 110b, and the medical professional 115. For example, the triage engine 130 may sort and prioritize received questions to generate a response.

In some implementations, the triage engine 130 may retrieve medical content to answer the questions from an unstructured database 135 and a structured database 140. As shown, the structured database 140 includes electronic medical records (EMR 145). For example, the EMR 145 may include a name, medical history, discharge records, and/or other personal identification of a user. The unstructured database 135 includes medical media content (MMC 150). For example, the MMC 150 may include video messages, audio messages, and/or text messages from the medical professional 115 to the patient 110a.

In various implementations, the information retrieved from the unstructured database 135 and the structured database 140 may include protected health information (PHI). For example, the PHI may include individually identifiable information of physical or mental health, health care services, or payment for medical services of a person. PHI may, for example, include a patient's name, address, date of birth, social security number, medical record number, and any other information that can be used to identify the patient. PHI is protected by the Health Insurance Portability and Accountability Act (HIPAA) Privacy Rule. In some examples, data containing PHI may be prohibited to be transmitted into an unsecured domain 101.

The triage engine 130, for example, may route the data (e.g., the EMR 145 and the MMC 150) retrieved from the unstructured database 135 and the structured database 140 to various generative modules based on the routing rules 125. For example, the routing rules 125 may include predetermined privacy rules based on an identity of a user and/or a relationship between the user and a patient. For example, when a question is received from a caretaker or a friend of the patient 110a, the routing rules 125 may prevent the triage engine 130 to retrieve personal messages to the patient 110a from the unstructured database 135.

In this example, the HIGS 105 includes an artificial intelligence model (AIM 155). The AIM 155 includes an internal LLM (internal LLM 160). In some implementations, the internal LLM 160 may be used to identify a type of a question based on the content of the question. For example, based on a type of question (e.g., simple query of a future appointment data or other information that may be resolved within the MRIS 100), the routing rules 125 may route the triage engine 130 to use the internal LLM 160 to generate an answer message.

In some implementations, the response generator 120 may use one or more external LLM models to answer questions in the unsecured domain 101 using data retrieved from the unstructured database 135 and the structured database 140 even if the data may include sensitive data (e.g., PHI). In this example, the unsecured domain 101 includes a PHI approved LLM 165 and a public LLM 170. For example, the PHI approved LLM 165 may be a regulated LLM approved by HIPAA. For example, the PHI approved LLM 165 may be operated under a HIPAA Business Associate Agreement (BAA) to ensure compliance on PHI security and overall HIPAA compliance. The public LLM 170, for example, may be operating without PHI approved procedure. For example, it would be prohibited to supply PHI to the public LLM 170. In some examples, however, the public LLM 170 may include more information and/or be trained with larger data than the PHI approved LLM 165. For example, the public LLM 170 may generate answers to more problems for the MRIS 100.

In this example, the HIGS 105 includes a sanitation engine 175 to remove sensitive data. For example, after retrieving content from the unstructured database 135 and/or the structured database 140, the triage engine 130 may use the sanitation engine 175 to remove sensitive data (e.g., PHI) from the retrieved content. In some implementations, the sanitation engine 175 may remove PHI from the retrieved content. In some implementations, the sanitation engine 175 may process the retrieved content by first transcribing media (e.g., a video content, an audio content) and then remove PHI from the transcription.

The HIGS 105 includes an external LLM interfacing engine (ELLMIE 180) to communicate with LLMs in the unsecured domain 101. For example, the HIGS 105 may use the ELLMIE 180 to transmit questions answers (e.g., including text, images, audio, video, transcription, translation, closed captioning, or a combination thereof) to the PHI approved LLM 165 and the public LLM 170. For example, the HIGS 105 may use the ELLMIE 180 to receive answers (e.g., text, images, audio, video, transcription, translation, closed captioning, or a combination thereof) from the PHI approved LLM 165 and the public LLM 170.

As shown, the ELLMIE 180 generates a question answer package (QAP 185). For example, the QAP 185 may include a sanitized question generated based on a question received from a user (e.g., the patient 110a, the user 110b, the medical professional 115) and content retrieved from the unstructured database 135 and the structured database 140. In some implementations, the ELLMIE 180 may use the AIM 155 to reframe the question based on a designated LLM (e.g., the PHI approved LLM 165 or the public LLM 170) in the unsecured domain 101. For example, the reframed question may be generated to improve a quality of an answer received from the unsecured domain 101.

In some implementations, the ELLMIE 180 may generate the QAP 185 as a secured LLM input array. For example, the ELLMIE 180 may associate a secured user input (e.g., a desensitized user input by the sanitation engine 175 applying the sanitization rules 265) and the secured media objects together to, for example, populate the secured LLM input array without the sensitive data. For example, the ELLMIE 180 may advantageously provide a secure input to the public LLM 170 and/or the PHI approved LLM 165 to generate a human-readable response.

The ELLMIE 180 also receives the answer from the unsecured domain 101. For example, the ELLMIE 180 may include an application user interface (API) to communicate with the PHI approved LLM 165 and the public LLM 170. In some implementations, the received answer may be relayed to the triage engine 130. The triage engine 130, for example, may use the sanitation engine 175 to re-associate sensitive data (e.g., the PHI) into the received answer. For example, the re-associated answer may advantageously be more personalized and easier to follow for a requestor. Accordingly, for example, the HIGS 105 may advantageously regenerate a human-readable response received from various LLM without sensitive data to include at least some of the sensitive data associated with the patient 110a. In some examples, the HIGS 105 may generate a sensitized response that is the direct response to a user input originally received from the user devices.

In some implementations, the triage engine 130 may also use the AIM 155 to reframe the answer to adjust a tone and languages of an answer based on the requestor's profile (e.g., language, role, knowledge, history, relationship with the patient 110a). For example, when the triage engine 130 receives a request from the medical professional 115, the triage engine 130 may generate an answer with more professional terminology and in a shorter format to save time for the medical professional 115. For example, when the requestor is the patient 110a or the user 110b, the triage engine 130 may generate a simpler answer and may include more media content to explain the answer to the requestor.

Various embodiments may, for example, advantageously provide a technical solution to the problem of using public domain LLM to resolve health related questions from users. For example, a customer service personnel processing a user's question about, for example, caring instructions after being discharged from a hospital post-surgery may be required to manually check and remove all PHI from the question before transmitting the question to the public domain LLM. For example, after receiving the answer, the customer service personnel may need to manually reinsert and compose an answer tailored to the user's knowledge and role. Additionally, the customer service personnel may also need to decide between various LLMs based on past performance to decide where to route the received question. Various checking and generative tasks may seriously limit the number of requests possibly processed by one customer service person. In some examples, the advantages of using a LLM, where a large number of answers may be generated reliably and accurately, may be distinguished due to a need to be compliant to the HIPAA.

In various implementations, the MRIS 100 may, for example, advantageously provide a technological solution to a technical problem arising from using external LLMs to answer questions with sensitive content. As an illustrative example without limitation, after a request/question is received from a requestor at the triage engine 130, the triage engine 130 may dynamically generate a request to the routing rules 125. For example, based on a suggested answer route (e.g., using the internal LLM 160, the PHI approved LLM 165, or the public LLM 170), the triage engine 130 may generate a question using the sanitation engine 175 and/or the ELLMIE 180.

In various implementations, the MRIS 100 may, for example, advantageously provide a technological solution to a technical problem arising from overprotecting privacy of patients resulting in non-personal replies from automatic response. For example, the sanitation engine 175 may resensitize a response by incorporating specific patient-related data back to the response. For example, the sanitation engine 175 may advantageously tailor the final response according to the context of the original query, and/or an association between the inquirer and the patient.

In various implementations, the MRIS 100 may, for example, advantageously provide a technological solution to a technical problem arising from incorporating multiple data sources and LLMs for answering natural language queries from users. For example, the MRIS 100 may integrate data from both the unstructured database 135 and the structured database 140 to generate a combined answer in response to the natural language query from the user without compromising data privacy.

In various implementations, the MRIS 100 may, for example, advantageously provide a technological solution to a technical problem arising from dynamically adjusting privacy levels based on the context and user relationship. The MRIS 100 may be configured to, for example, dynamically adjust a level of desensitization and resensitization based on predefined rules. For example, the rules may be configured to provide a privacy level that is appropriate for the context and relationship between the inquirer and the patient. Various implementations are further described with reference to FIG. 15.

In some implementations, the routing rules 125 may route a request as a function of retrieved data contents, question, query type, a requestor's profile, predetermined privacy rules, and/or historical performance of available LLMs. For example, the MRIS 100 may provide a technical solution to the problem of selectively routing questions to an external LLM to obtain optimized results. Various embodiments of routing methods are described with reference to FIG. 8.

If the question is to be sent to the unsecured domain 101, the question may be sanitized using the sanitation engine 175. Also, the question may also include content, retrieved from the unstructured database 135 and/or the structured database 140 to answer the question. In some implementations, the data may also be sanitized using the sanitation engine 175. For example, the ELLMIE 180 may generate a QAP 185 using the sanitized question and content to the PHI approved LLM 165 or the public LLM 170. In some implementations, the QAP 185 may also include some linking identifications or metadata to link a received answer the unsecured domain 101 back to the requestor.

In some implementations, the MRIS 100 may provide a technical solution to the problem of generating a personalized answer to a user after removing personal data from the question to be used in the external LLM. For example, upon receiving an answer from the unsecured domain 101, the ELLMIE 180 may use the sanitation engine 175 to re-associate the received answer with the requestor (e.g., the patient 110a). In some implementations, the triage engine 130 may also save the answers to the unstructured database 135 as part of the unstructured medical record of the patient 110a.

In various implementations, a MIRS may include a routing engine (e.g., the triage engine 130) that route a received question from a user (e.g., the patient 110a, the user 110b, or the medical professional 115) to external LLM (e.g., the PHI approved LLM 165, or the public LLM 170). Based on identified sensitive information, the MIRS may include a sensitization engine (e.g., the sanitation engine 175) to sanitize both structured data (e.g., the EMR 145) and unstructured data (e.g., the MMC 150). For example, the MIRS may include an auto-chat function (e.g., the internal LLM 160) to reframe the received question to advantageously improve efficiency and quality of an answer received from the external LLM. For example, the internal LLM 160 may also reframe and/or interpret a received answer before generating an answer package to the user to advantageously provide improved user experience.

In various embodiments, a medical records interaction system (e.g., the MRIS 100) may be configured to generate a question package (e.g., the QAP 185) by desensitizing sensitive data from an inquiry received from an inquirer about a patient and electronic health records of the patient before transmission to an inquiry answering system including public LLMs, (e.g., the public LLM 170). For example, the medical records interaction system may be configured to generate an answer to the inquiry by resensitizing a reply received from the inquiry answering system.

Figure 2:
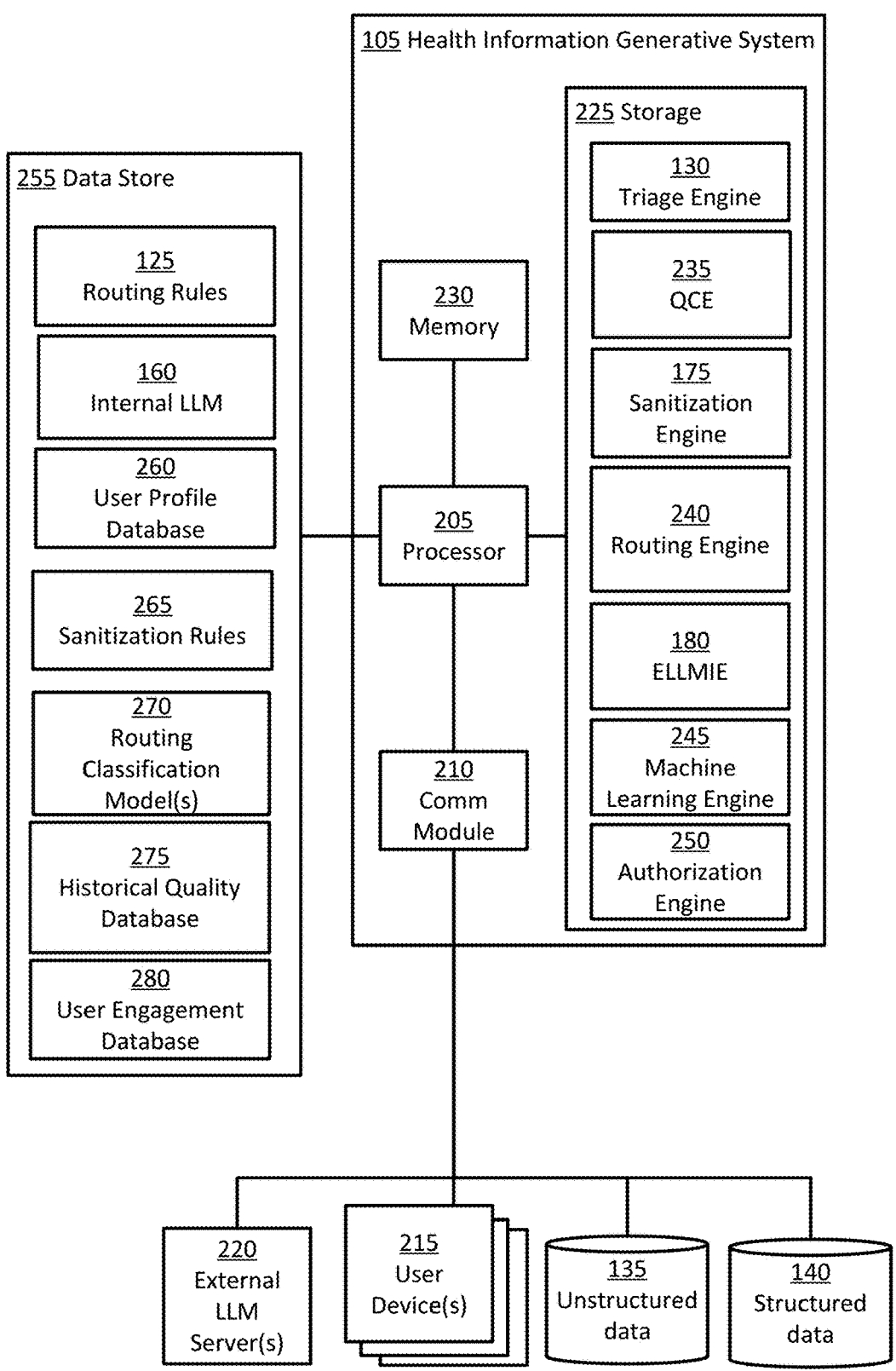
FIG. 2 is a block diagram depicting an exemplary health information generative system (HIGS).

FIG. 2 is a block diagram depicting an exemplary HIGS 105. The HIGS 105 includes a processor 205. The processor 205 may, for example, include one or more processors. The processor 205 is operably coupled to a communication module 210. The communication module 210 may, for example, include wired communication. The communication module 210 may, for example, include wireless communication. In the depicted example, the communication module 210 is operably coupled to user device(s) 215. For example, the user device 215 may include mobile devices of users and/or desktop computers of users. In the depicted example, the communication module 210 is operably coupled to the unstructured database 135 and the structured database 140. For example, the communication module 210 may retrieve structured data (e.g., the EMR 145) and unstructured data (e.g., the MMC 150) from the structured database 140 and the unstructured database 135, respectively.

The communication module 210 is operably coupled to one or more external LLM external LLM server(s) 220. For example, the external LLM server(s) 220 may include the PHI approved LLM 165 and the public LLM 170. For example, the communication module 210 may transmit the QAP 185 to the external LLM server(s) 220. For example, the communication module 210 may receive an answer to the QAP 185 from the external LLM server(s) 220.

The processor 205 is operably coupled to a memory module 230. The memory module 230 may, for example, include one or more memory modules (e.g., random-access memory (RAM)). The processor 205 includes a storage module 225. The storage module 225 may, for example, include one or more storage modules (e.g., non-volatile memory). In the depicted example, the storage module 225 includes the triage engine 130, a question classifying engine (QCE 235), the sanitation engine 175, a routing engine 240, the ELLMIE 180, a machine learning engine 245, and an authorization engine 250. The processor 205 further operably coupled to a data store 255. The data store, as depicted, includes the routing rules 125, the internal LLM 160, a user profile database 260, sanitization rules 265, a routing classification model(s) (RCM 270), a historical quality database 275, and a user engagement database 280.

The triage engine 130, for example, may receive an inquiry from the user device 215. For example, the triage engine 130 may prepare an answer to the inquiry by dynamically gathering data to answer the inquiry. For example, the triage engine 130 may process the inquiry by retrieving health content from the unstructured database 135 and the structured database 140. For example, the triage engine 130 may retrieve a medical record associated with the inquiry, a relationship of a requestor associated with the user device 215 to a patient (e.g., the patient 110a). For example, the triage engine 130 may use the QCE 235 to classify a type of the inquiry before gathering information from the unstructured database 135 and the structured database 140.

The authorization engine 250, for example, may be used to restrict the health content to be retrieved by the triage engine 130 based on an identification of the user device 215. For example, the authorization engine 250 may retrieve an identification of the user device 215 using the user profile database 260. For example, if the user device 215 is associated with a caretaker of the patient 110a, the authorization engine 250 may restrict certain health content (e.g., medical diagnosis records, images, private conversations with medical professionals) from being retrieved to answer a question from a caretaker's device.

In some implementations, the triage engine 130 may use the routing engine 240 to determine a LLM to be used to generate an answer to the inquiry. For example, the routing engine 240 may select a LLM (e.g., the internal LLM 160, the PHI approved LLM 165, the public LLM 170) using the routing rules 125 and the RCM 270. The RCM 270, for example, may be a trained classification model to select one or more combinations of LLM to be used as a function of the received question and the user profile database 260 associated with the user device 215 that transmits the question. For example, a question related mostly to private data without the need for public domain information may be answered using the internal LLM 160. For example, the public LLM 170 may be selected to answer a general question about translating or explaining a term. In some implementations, the RCM 270 may include select to use multiple LLMs. For example, the triage engine 130 may combine answers received from the multiple LLMs to generate an answer to the user device 215.

Based on the selection, for example, the routing rules 125 may include rules and/or steps to route the health content to use the selected LLM. For example, if the internal LLM 160 is selected, the routing rules 125 may include steps to remove sensitive content from the answer based on a permission level of the requestor's device while keeping the question unsensitized to be used by the internal LLM 160. In some examples, if an external LLM is selected and the requestor is the patient 110a himself, the routing rules 125 may include steps to first remove sensitive content from the question to be sent to the external LLM, and then reassociate personal information to an answer before transmitting to the patient 110a to improve accuracy and relatability of the answer.

In some implementations, the triage engine 130 may also use the internal LLM 160 to analyze content of a received answer from the unsecured domain 101. For example, the triage engine 130 may use the internal LLM 160 to identify a type of an answer (e.g., an answer for an urgent medical situation, an answer for a general inquiry about daily care)

based on the analyzed content. For example, based on an identified type of a received answer, the triage engine 130 may generate a more accurate and/or relatable answer for a requestor.

In some implementations, based on the selection, the triage engine 130 may use the sanitation engine 175 to remove personal identifying information from the health content retrieved from the unstructured database 135 and the structured database 140. For example, the sanitation engine 175 may use the sanitization rules 265 to remove sensitive data from the health content. In some implementations, the sanitization rules 265 may include predetermined privacy rules. For example, the predetermined privacy rules may include rules from the HIPAA. For example, the sanitization rules 265 may identify and remove any sensitive information in the EMR 145 and/or other media content (e.g., text messages, video, audio messages). In some implementations, the sanitation engine 175 may also use data from the user profile database 260 for scanning sensitive data from the health content. For example, the sanitation engine 175 may identify a current location and eating habits of the user from the user profile database 260.

In some implementations, the triage engine 130 may use the ELLMIE 180 to interface with the external LLM server(s) 220. For example, the ELLMIE 180 may generate the QAP 185 to be transmitted to a selected external LLM server. In some implementations, the ELLMIE 180 may use the internal LLM 160 to generate an intermediate question that is more efficient to the selected external LLM server. For example, multiple intermediate questions may be generated based on multiple selected external LLM servers (e.g., a question A generated for the PHI approved LLM 165 and a question B generated for the public LLM 170, and both questions A and B are related to a same question received from a user device.).

In some implementations, the ELLMIE 180 may selectively include PHI in the QAP 185. For example, the ELLMIE 180 may use the internal LLM 160 to mask or vary PHI (e.g., by changing the symptom slightly) in the question to generate the QAP 185. For example, the ELLMIE 180 may advantageously improve accuracy of the answer.

The machine learning engine 245 may be used to train the internal LLM 160 and the RCM 270, for example. In some implementations, the machine learning engine 245 may use the historical quality database 275 and the user engagement database 280 to train the internal LLM 160 and the RCM 270. For example, the historical quality database 275 may include an object evaluation from medical professionals and users regarding a quality vector of each answer provided by the HIGS 105. The quality vector, in some implementations, may include medical data accuracy, answer tone, quality of words, responding speed, and other objective training factors.

The user engagement database 280, for example, may include subjective training factors. For example, the user engagement database 280 may measure a time of engagement of a user in communicating with the HIGS 105. In some examples, the user engagement database 280 may include a number of follow up questions from a user after an initial answer is provided. For example, the user engagement database 280 may include a detection of emotion of a user based on further responses received from the user after an initial answer is given. For example, if it is detected (e.g., from a further conversation, from direct user feedback) the user is depressed after a blunt answer is given, the machine learning engine 245 may train the internal LLM 160 to generate an alternative less gloomy answer in similar situations. Various embodiments of machine learning methods and systems are described with reference to FIGS. 4-5.

Figure 3:
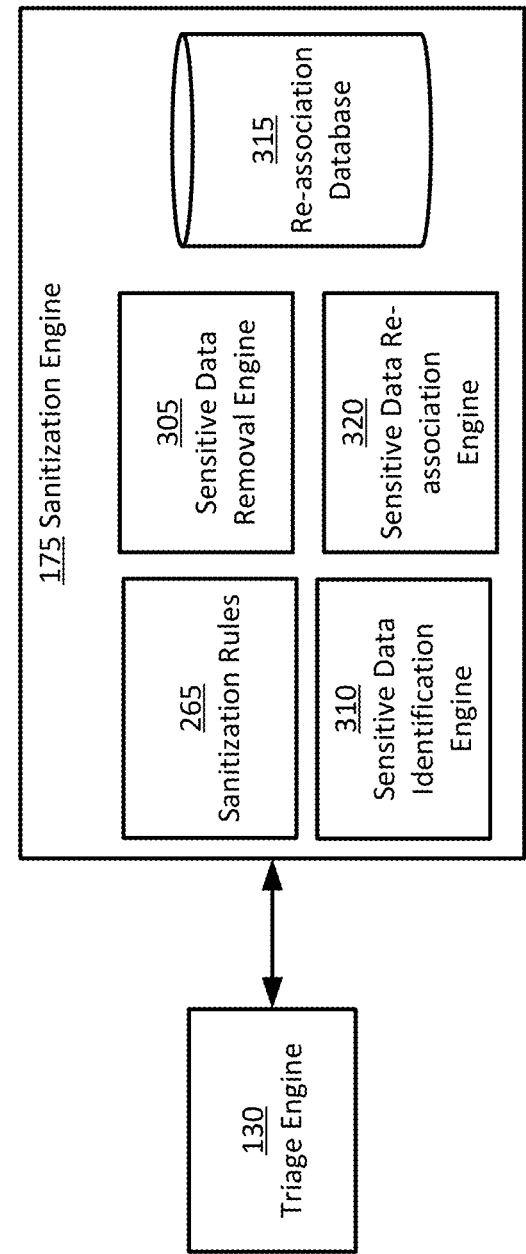
FIG. 3 is a block diagram depicting an exemplary sanitization engine.

FIG. 3 is a block diagram depicting an exemplary sanitization engine. In this example, the sanitation engine 175 is operably coupled to the triage engine 130. For example, health content retrieved from the unstructured database 135 and the structured database 140 may be transmitted to the sanitation engine 175 from the triage engine 130. The triage engine 130 may, for example, receive a sanitized content from the sanitation engine 175.

In this example, the sanitation engine 175 includes a sensitive data removal engine (SDRE 305). For example, the SDRE 305 may use the sanitization rules 265 to remove PHI from a received health content. For example, the SDRE 305 may transcribe a received video message and remove personal identifying information (e.g., name, phone number, address, medical record numbers, any digital identifiers) from the transcription.

In this example, the SDRE 305 may use a sensitive data identification engine 310 to identify the sensitive data based on the sanitization rules 265. In some implementations, the SDRE 305 may replace the sensitive data with generic data. For example, the SDRE 305 may replace a name with a generic name (e.g., John Doe). In some examples, other sensitive information may be replaced or fuzzified using the SDRE 305.

In some implementations, removed sensitive information may be stored in the re-association database 315. For example, the re-association database 315 may include a mapping between a question and sensitive information removed from the question. For example, the sanitation engine 175 may assign a unique identifier for each question and the health information associated with the question. For example, each removed and/or replaced information may be associated with a removal identifier.

The sanitation engine 175, in this example, includes a sensitive data re-association engine 320. In some implementations, the sanitation engine 175 may receive one or more answers from the triage engine 130 associated with a question. For example, the one or more answers may be received from multiple LLMs (e.g., the internal LLM 160, the PHI approved LLM 165, and the public LLM 170). For example, the sensitive data re-association engine 320, upon retrieving relevant sensitive information from the re-association database 315 based on a question identification, may re-insert sensitive information (e.g., personal information) into each of the multiple answers. Accordingly, the answers may advantageously be more relatable and engaging, for example.

Figure 4:
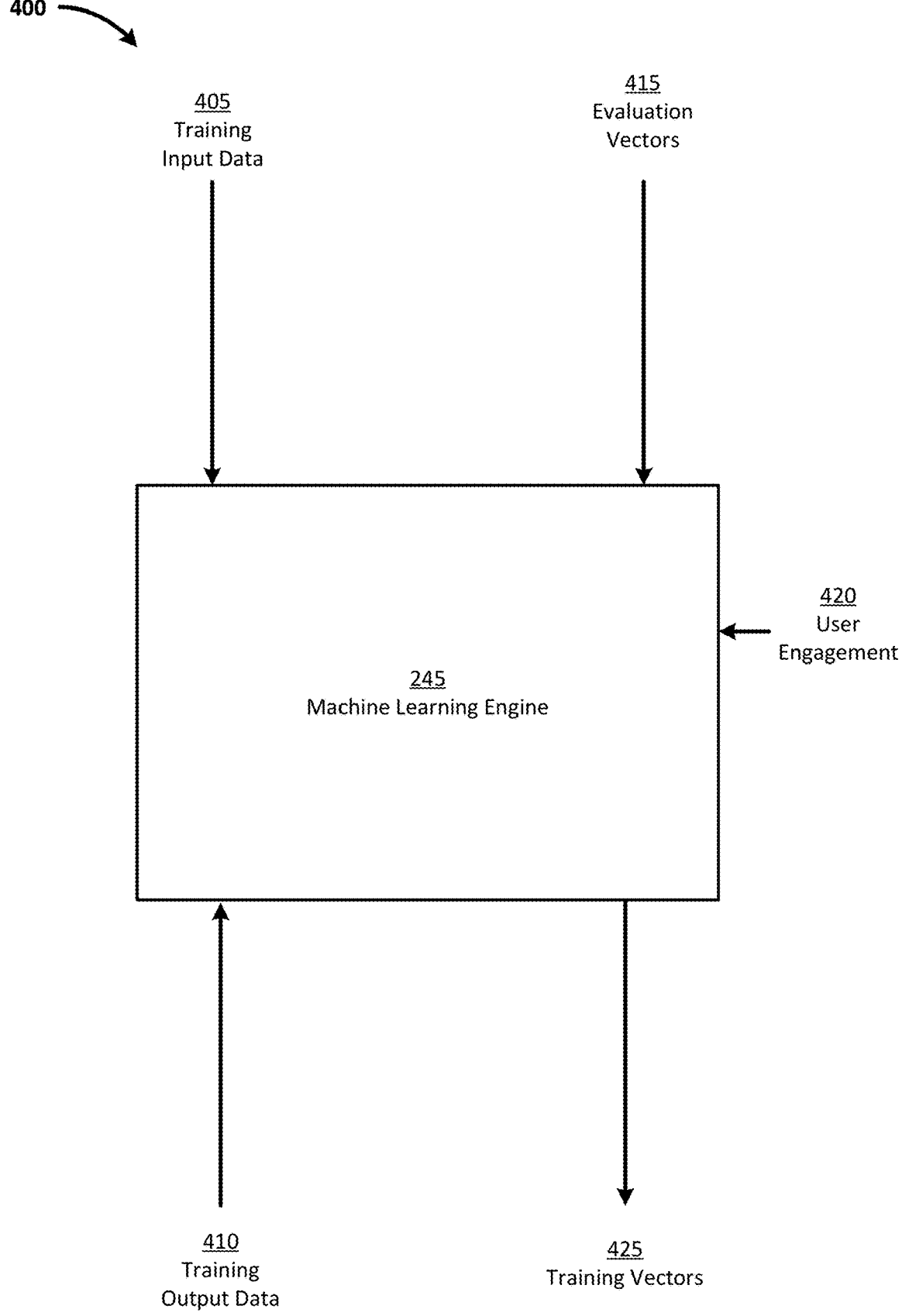
FIG. 4 depicts an exemplary machine learning engine for training internal machine learning models.

FIG. 4 depicts an exemplary machine learning engine for training internal machine learning models. In a training system 400, the machine learning engine 245 may train one or more machine learning models. For example, the machine learning models may include the RCM 270. For example, the machine learning models may include the internal LLM 160.

The machine learning model may, by way of example and not limitation, include a neural network model. The neural network model may include, for example, recurrent neural network (RNN) and/or deep neural network (DNN). The machine learning model may, for example, include an ensemble model. Different neural network models may be selected. The number of the model layers (e.g., the hidden neurons) may also be determined based on, for example, the complexity of content descriptions and/or attributes.

A set of training data is applied to the machine learning engine 245 to train the machine learning model. The training data includes a training input data 405 and a training output data 410. The training input data 405 may include, for example, a set of questions. The training input data 405 may include, for example, historical questions received by the HIGS 105.

The set of training output data 410 may include historical answers corresponding to the questions in the training input data 405. The training output data 410 may, for example, be selected to correspond to the training input data 405. In some implementations, the training input data 405 and the training output data 410 may be selected based on the user profile database 260 associated with the question. For example, the machine learning engine 245 may be used to train a response to a selected type of requestor (e.g., from caretaker, from medical professionals, from patients oneself). In some examples, the training input data 405 and the training output data 410 may be selected based on response time (e.g., answers generated with a delay out of tolerance may be selected to be retrained to improve response time).

In some embodiments, before training, a set of testing data (including testing input data and the testing output data) may be divided from the training data. After a machine learning model is trained (e.g., the internal LLM 160 and/or the RCM 270), the testing data may be applied to the trained model to test the training accuracy of the model. For example, the trained model may receive the testing input data and generate an output data in response to the testing input data. The generated output data may be compared with the testing output data to determine the prediction accuracy (e.g., based on a predetermined criterion(s) such as a maximum error threshold). In some embodiments, one or more models (e.g., neural network models) may be cascaded together. The cascaded model may be trained and tested.

In this example, an evaluation vector 415 may be used to evaluate the trained machine learning model. For example, the evaluation vector 415 may include objective factors including speed of response, a cost of generating the response (e.g., service fee, energy usage, machine depreciation cost), preference of a service provider selected by a requestor, and historical performance of one or more LLMs.

In this example, the training system 400 includes user engagement input 420. For example, the user engagement input 420 may be generated from the user engagement database 280. For example, the user engagement input 420 may be generated corresponding to a question and answer training set. For example, the machine learning engine 245 may use the user engagement input 420 to evaluate a trained machine learning model.

After a training process, the machine learning engine 245 generates training vectors 425, for example. In some implementations, the training vectors 425 may be used to update weighting or other parameters of the trained machine learning models (e.g., the internal LLM 160, the RCM 270).

FIG. 5 depicts an exemplary method 500 of training a content characterization engine. For example, the method 500 may be performed by the machine learning engine 245 as described with reference to FIG. 4. The method 500 begins when a signal is received to start a training process of a selected machine learning model in step 505. For example, training in a machine learning model may be triggered by an administrative user. For example, the administrative user may select to train the internal LLM 160 periodically (e.g., weekly, monthly, yearly). For example, the HIGS 105 may be automatically triggered to retrain the internal LLM 160 and/or the RCM 270 when a quality score of either or both of the models drops below a predetermined threshold.

In step 510, a training data set is generated. For example, the training data set may be generated from the historical quality database 275. For example, the training data set may include the training input data 405 and the training output data 410. Next, in step 515, user engagement vectors are retrieved corresponding to the training data set. For example, the user engagement input 420 of each of the training input data 405 may be retrieved from the user engagement database 280.

In step 520, a testing data set is generated. For example, the machine learning engine 245 may generate the testing data set from the training input data 405 and the training output data 410. After the training data set and the testing data set are generated, in step 525, an updated model is generated. For example, the machine learning engine 245 may use the training input data 405 and the training output data 410 to train a machine learning model (e.g., the internal LLM 160 and/or the RCM 270). In step 530, the updated model is evaluated by assigning a score based on objective evaluation vectors and the user engagement vectors. For example, the machine learning engine 245 may generate a quality score for an updated machine learning model based on objective factors (e.g., speed, accuracy, proper wordings) and/or subjective factors (e.g., estimated user engagement, relatedness).

In a decision point 535, it is determined whether the score is within tolerance. For example, the tolerance may be an overall score threshold. For example, the tolerance may be a set of quantitative thresholds that the updated model must meet. If the score is not within tolerance, in step 540, parameters of the training model are updated based on the score, and the step 525 is repeated. For example, the machine learning engine 245 may adjust a step size, epoch size, testing and training data sets to re-train the machine learning model. If the score is within tolerance, an update vector for the selected machine learning model is generated in step 545, and the method 500 ends. For example, the machine learning engine 245 may generate the training vectors 425 after training to update the internal LLM 160 and/or the RCM 270.

Figure 6:
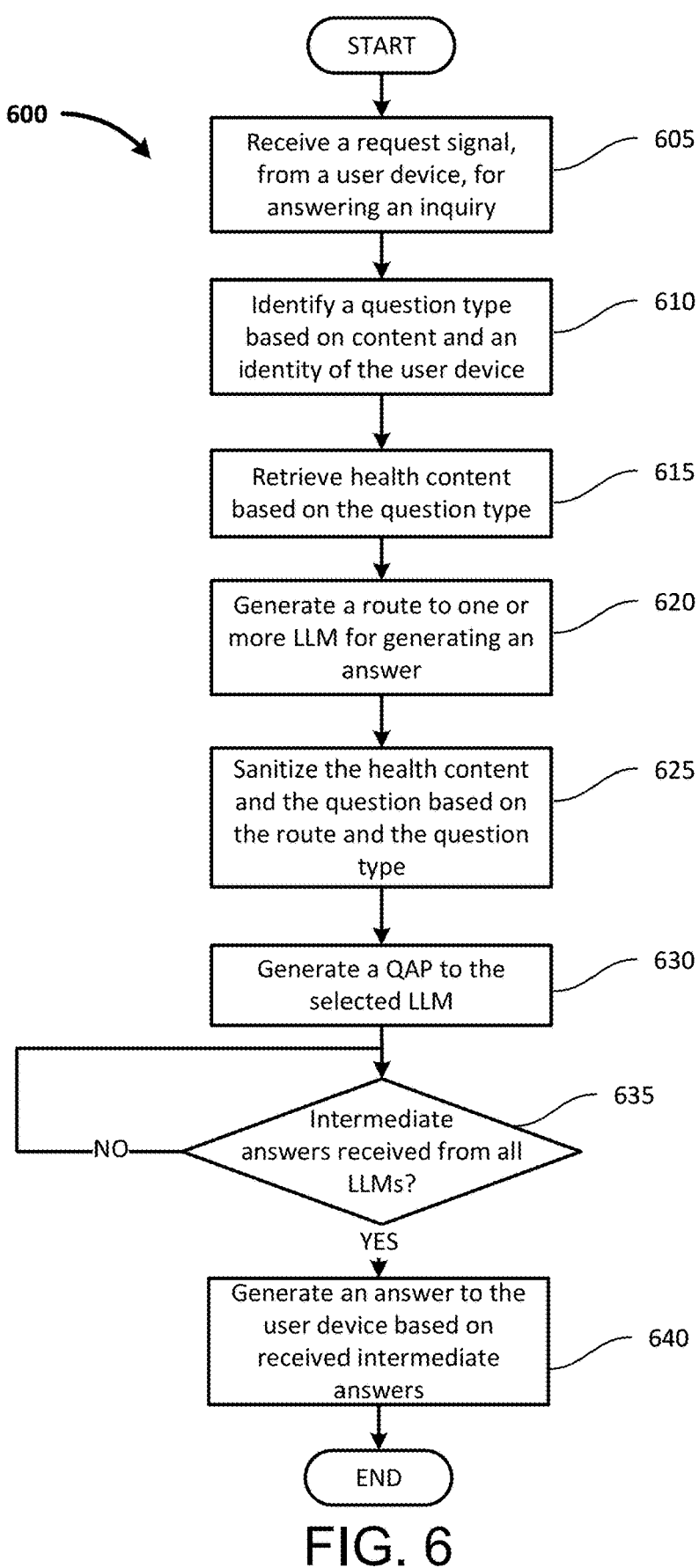
FIG. 6 is a flowchart illustrating an exemplary inquiry response generation method.

FIG. 6 is a flowchart illustrating an exemplary inquiry response generation method 600. For example, the method 600 may be performed by the response generator 120 as described with reference to FIG. 1. For example, the response generator 120 may use the inquiry response generation method 600 to generate a response to a user device (e.g., the mobile device 111a, the mobile device 111b). In this example, the method 600 begins in step 605 when a request signal is received from a user device for answering an inquiry. For example, the request signal may be generated by an application in a mobile device. In some implementations, the request signal may be generated by a server upon receiving an inquiry from the mobile device.

In step 610, a question type is identified based on content and an identity of the user device. For example, the response generator 120 may use the user profile database 260 to identify an identity of the user device. For example, the response generator 120 may use the QCE 235 to identify the question type based on the content of the received inquiry.

Next, in step 615, health content is retrieved based on the question type. For example, the response generator 120 may use the triage engine 130 to retrieve health content based on the question type from the unstructured database 135 and the structured database 140. A route to one or more LLM for generating an answer is generated in step 620. For example, the triage engine 130 may select one or more LLM to generate an answer to a question based on the routing rules

125. In step 625, the health content and the question are sanitized based on the route and the question type. For example, the triage engine 130 may use the sanitation engine 175 to remove private information based on the selected LLM and predetermined privacy rules.

In step 630, a QAP is generated to the selected LLM. For example, the response generator 120 may use the ELLMIE 180 to generate the QAP 185 based on the selected LLM (e.g., the PHI approved LLM 165, the public LLM 170). In a decision point 635, it is determined whether intermediate answers are received from all LLMs. For example, the response generator 120 may wait for all of the selected LLM to return an answer for the transmitted QAP. If not all intermediate answers are received, the decision point 635 is repeated.

If all intermediate answers are received, an answer to the user device is generated based on the received intermediate answers in step 640, and the method 600 ends. For example, the response generator 120 may use the internal LLM 160 to aggregate one or more intermediate answers into one answer. For example, the response generator 120 may use the sanitation engine 175 to re-associate removed personal information to the answer.

Figure 7:
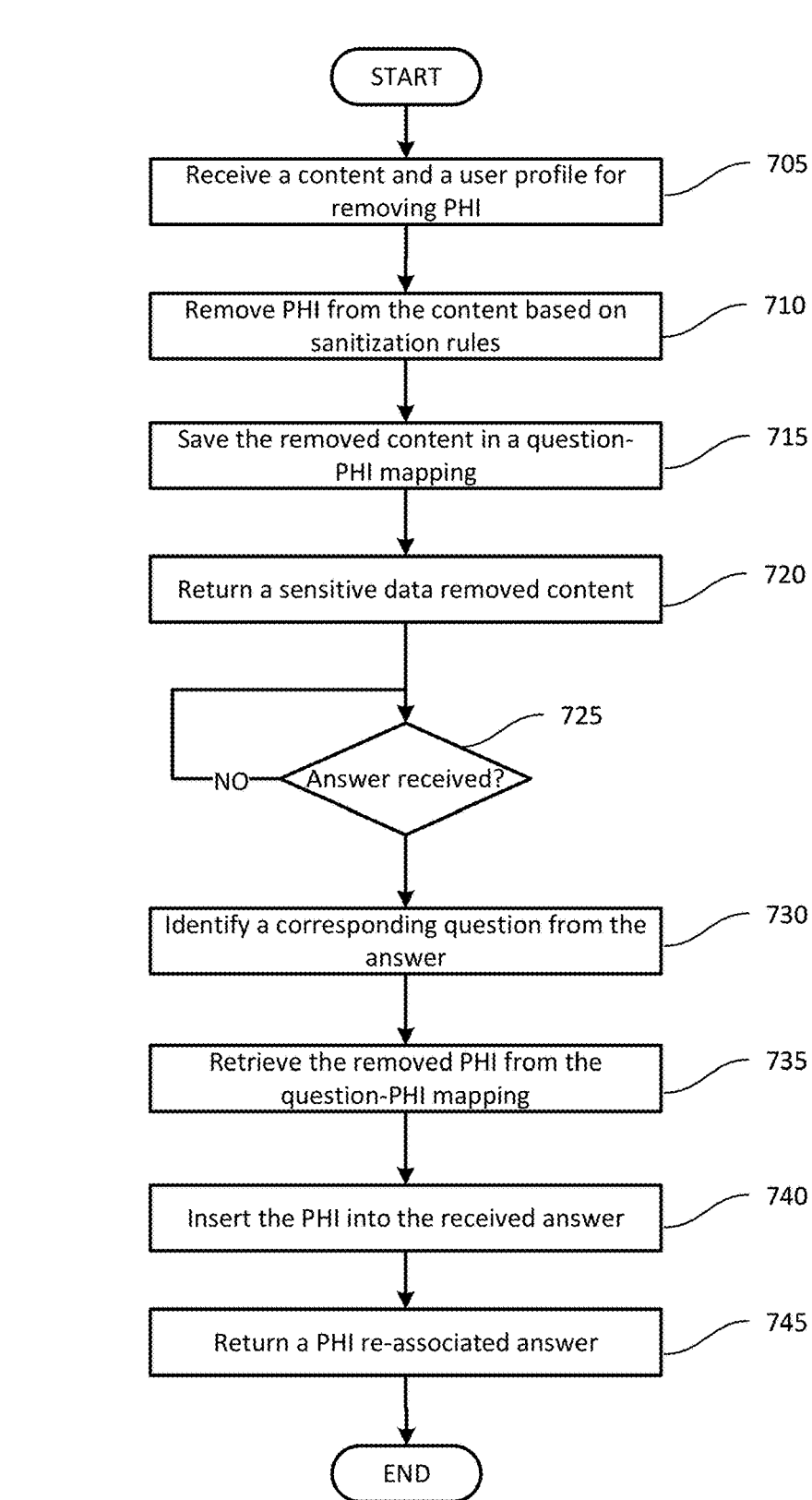
FIG. 7 is a flowchart illustrating an exemplary content sanitization and re-association method.

FIG. 7 is a flowchart illustrating an exemplary content sanitization and personalization method 700. For example, the sanitation engine 175 may perform the method 700 to remove sensitive information for transmitting a question into the unsecured domain 101. For example, the sanitation engine 175 may use the personalization method 700 to reassociate private information when intermediate answers are received from the unsecured domain 101.

In this example, the method 700 begins when a content and a user profile is received for removing PHI in step 705. For example, the content may include health content (e.g., the EMR 145, the MMC 150). In step 710, PHI is removed from the content based on sanitization rules. For example, the sensitive data identification engine 310 may identify the PHI from the content based on the sanitization rules 265. For example, based on the sanitization rules 265 the SDRE 305 may remove the identified PHI from the content. Next, in step 715, the removed content is saved in a question-PHI mapping. For example, the sanitation engine 175 may save the removed sensitive content into the re-association database 315.

In step 720, a sensitive data removed content is returned. For example, the sanitation engine 175 may return a "sanitized" content to the response generator 120 for transmitting to the unsecured domain 101. In a decision point 725, it is determined whether an answer is received. For example, the triage engine 130 may use the sanitation engine 175 to reassociate personal information into an answer received from the unsecured domain 101. If no answer is received, the decision point 725 is repeated.

If an answer is received, in step 730, a corresponding question is identified from the answer. For example, the triage engine 130 may transmit the answer with a question identifier. Next, the removed PHI is retrieved from the question-PHI mapping in step 735. For example, the sensitive data re-association engine 320 may retrieve sensitive information from the re-association database 315 based on a question identification. In step 740, the PHI is inserted into the received answer. For example, the re-association database 315 may insert the retrieved sensitive information into appropriate locations in the answer using the internal LLM 160. Next, a PHI re-associated answer is returned in step 745 and the method 700 ends. For example, a sensitive information re-associated answer may be returned to the triage engine 130.

Figure 8:
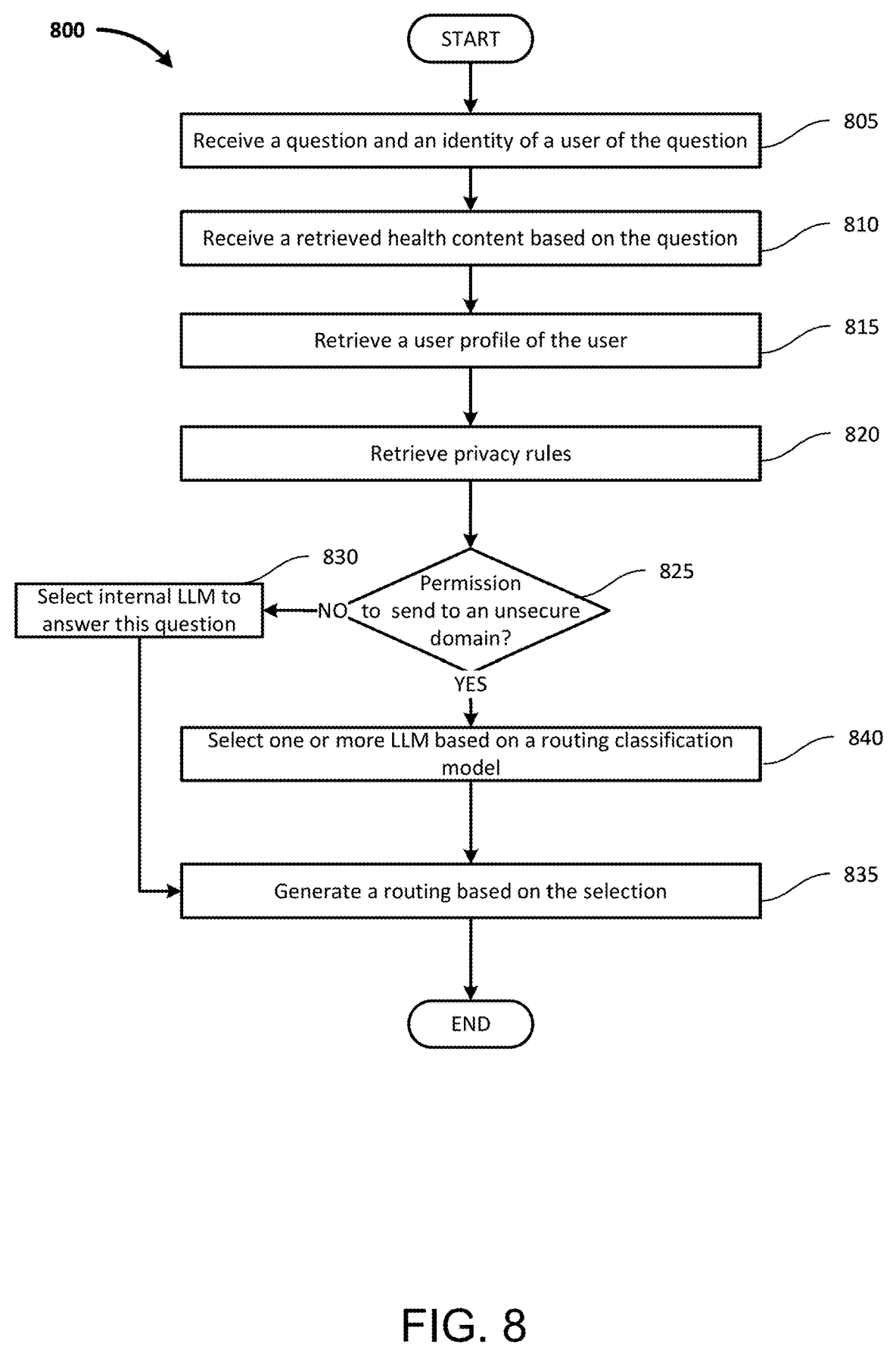

FIG. 8 is a flowchart illustrating an exemplary answer data package routing method. For example, the routing engine 240 as described in FIG. 2 may perform the method 800. The method 800 begins in this example when a question and an identity of a user of the question is received in step 805. For example, the triage engine 130 may transmit a question and a user identity to the routing engine 240. In step 810, a retrieved health content is received based on the question. For example, the triage engine 130 may retrieve the health content from the unstructured database 135 and the structured database 140 based on the question content and permission generated by the authorization engine 250.

Next, a user profile of the user is retrieved in step 815. For example, the routing engine 240 may retrieve the user profile from the user profile database 260. In step 820, privacy rules are retrieved. For example, the privacy rules are retrieved from the routing rules 125.

In a decision point 825, it is determined whether there is permission to send to unsecure domain based on the privacy rules. For example, a question about a personal information of the patient 110a may not be permitted to be transmitted to the unsecured domain 101. For example, it may be unpermitted to transmit a question when the question is about the exact payment amount for a surgery performed on a patient on an exact date.

If there is no permission to send the question to an unsecure domain, in step 830, an internal LLM is selected to answer this question. For example, the internal LLM 160 may be selected. In step 835, a routing based on the selection may be generated, and the method 800 ends. For example, the routing engine 240 may generate the routing of a question based on the selected LLM, the permission of the user, and the content of the question.

In the decision point 825, if there is permission to send the question not the unsecure domain, in step 840, one or more LLM may be selected based on a routing classification model, and the step 835 is repeated. For example, the routing classification model may include historical performance of available LLM. For example, the routing engine 240 may use the RCM 270 to select the LLMs.

Figure 9:
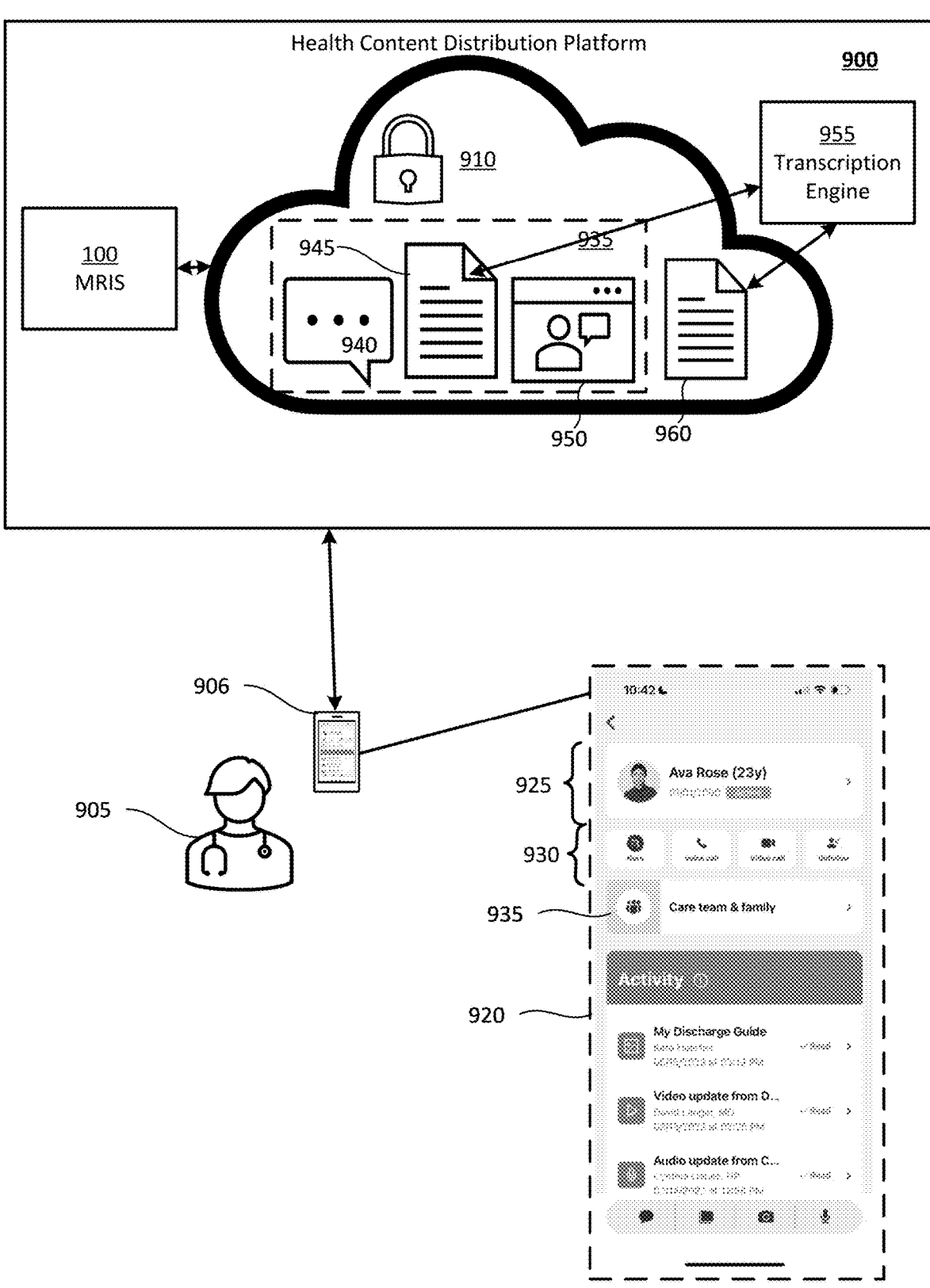
FIG. 9 depicts an exemplary user interface of an exemplary Health Content Distribution Platform (HCDP) on a user mobile device.

FIG. 9 depicts an exemplary user interface of an exemplary Health Content Distribution Platform (HCDP) on a user mobile device. In this example, a HCDP 900 includes the MRIS 100. The MRIS 100 is operably coupled to a and a secure cloud storage (SCS 910). The HCDP 900, for example, may authenticate a user's request for accessing health data. For example, the user may be a healthcare professional or a patient using the MRIS 100. In some implementations, the user may include other authorized individuals (e.g., government agents) who are authorized to access the electronic health records. For example, the SCS 910 may be a cloud storage capable of storing and transmitting digital content. In some implementations, the SCS 910 may be a secured private cloud storage accessible only by authenticated users of the HCDP 900.

The SCS 910, in this example, stores digital health content (DHC). As shown, the DHC includes a text message 940, an electronic health record 945, and a video content 950. In various implementations, other content may also be available. For example, the DHC may also include voice messages, health tips associated to a patient (e.g., the patient 110a, for example, of an exercise for recovering from a broken arm), schedule of next appointments at various clinics, information of prescribed medications, instant message contact list to related care providers, and/or other health related content associated with the patient. For example, the HCDP 900 may submit claims to insurance for a pre-operation procedure approval upon detection of an event (confirmation, discussion) of an operation procedure.

As shown, the HCDP 900 also includes a transcription engine 955. For example, the transcription engine 955 may transcribe some or all of the DHC into a transcription 960. For example, the transcription 960 may include a transcription of a voice instruction recorded by a doctor. For example, the transcription 960 may include a transcription of a video recorded by a pharmacist. In some implementations, the transcription engine 955 may also transcribe text into audio. For example, the transcription engine 955 may use LLM (e.g., the internal LLM 160 and/or the public LLM 170) to transcribe text and/or audio. In some implementations, the transcription engine 955 may also transcribe (e.g., describe) actions in a video.

In some implementations, the HCDP 900 may include an automatic process to automatically schedule a follow-up visit for the patient 110*a*. For example, the schedule may be automatically updated in the EMR 145 of the patient 110*a*. For example, the HCDP 900 may notify the patient 110*a* and/or a (referred) physician of the scheduled visit. For example, the HCDP 900 may automatically add access rights to (selected) records of the patient 110*a* to related patients' care team(s).

Various embodiments of the HCDP 900 are described with reference to U.S. patent application Ser. No. 17/806, 446, having common inventorship of this application, filed on Jun. 10, 2022, titled "Multi-Party Controlled Transient User credentialing for Interaction with Patient Health Data." This application incorporates the entire contents of the foregoing application herein by reference.

For example, the patient 110*a* may use the mobile device 111*a* to access the HCDP 900. For example, the mobile device 111*a* may access the HCDP 900 using methods and systems described in the U.S. patent application Ser. No. 17/806,446. In this example, a caretaker 905 is using a mobile device 906 to access a profile page 920 of a patient ("Ava Rose"). Upon successfully accessing the HCDP 900, the mobile device 906 may display a profile page 920.

As shown, the caretaker 905 may access a profile 925 of the patient. The profile page 920 also includes a list 930 of actions ("Nora", "Voice Call", "Video Call", "Unfollow") to interact with the profile. For example, the caretaker 905 may initiate a voice call to Ava. For example, the caretaker 905 may initiate a video call to Ava. For example, the caretaker 905 may unfollow Ava (e.g., when Ava ceases to be the caretaker 905's patient). The profile page 920 also includes a link 935 to view the care team and family of a patient. Also, the caretaker 905 may also use the profile page 920 to view recent activities of the patient. In some implementations, the profile page 920 or a similar layout of the profile page 920 may be generated based on a role (patient, family related to the patient, caretaking team member, nurse, insurance company staff) associated with the mobile device 906.

Figure 10A:
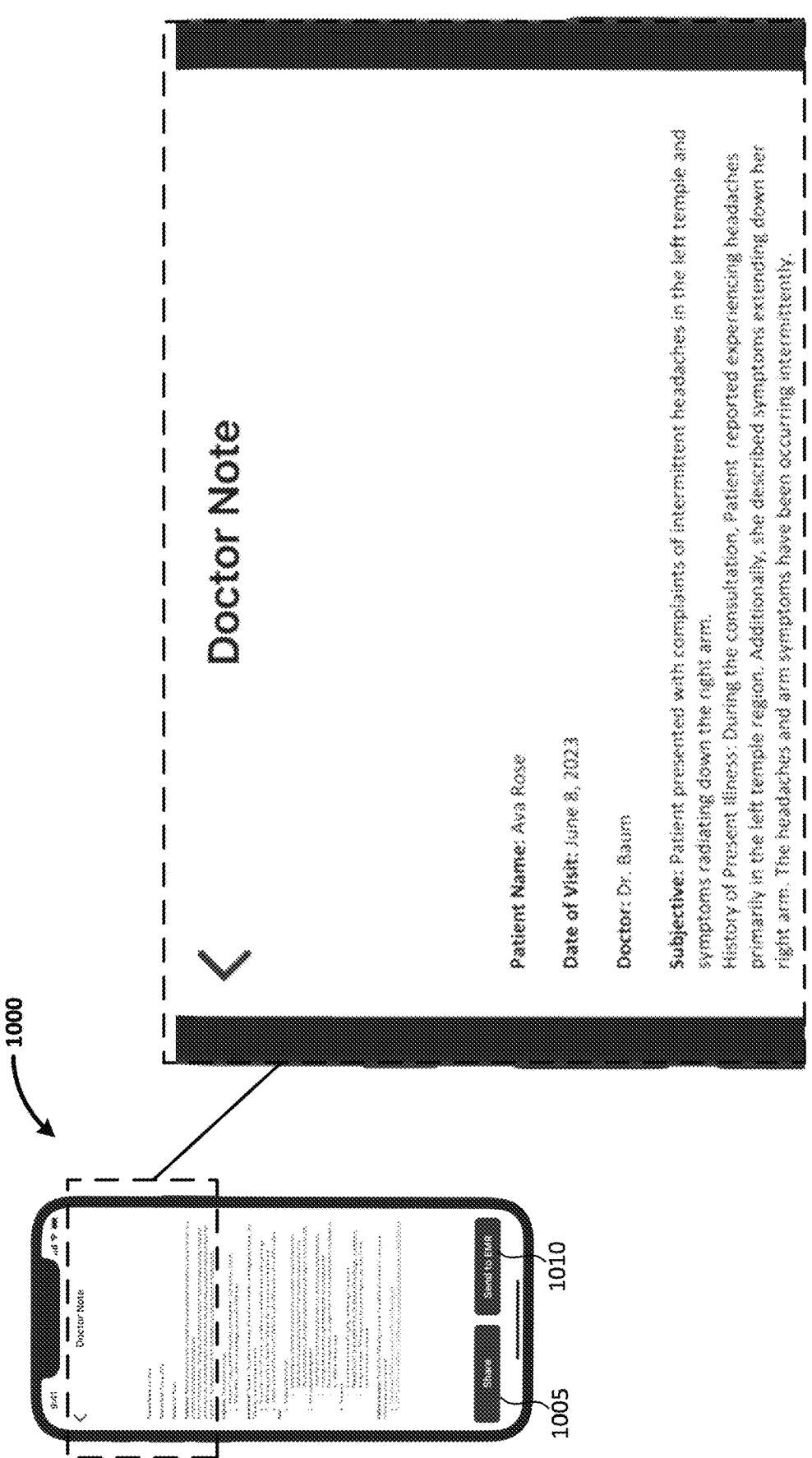
Figure 10C:
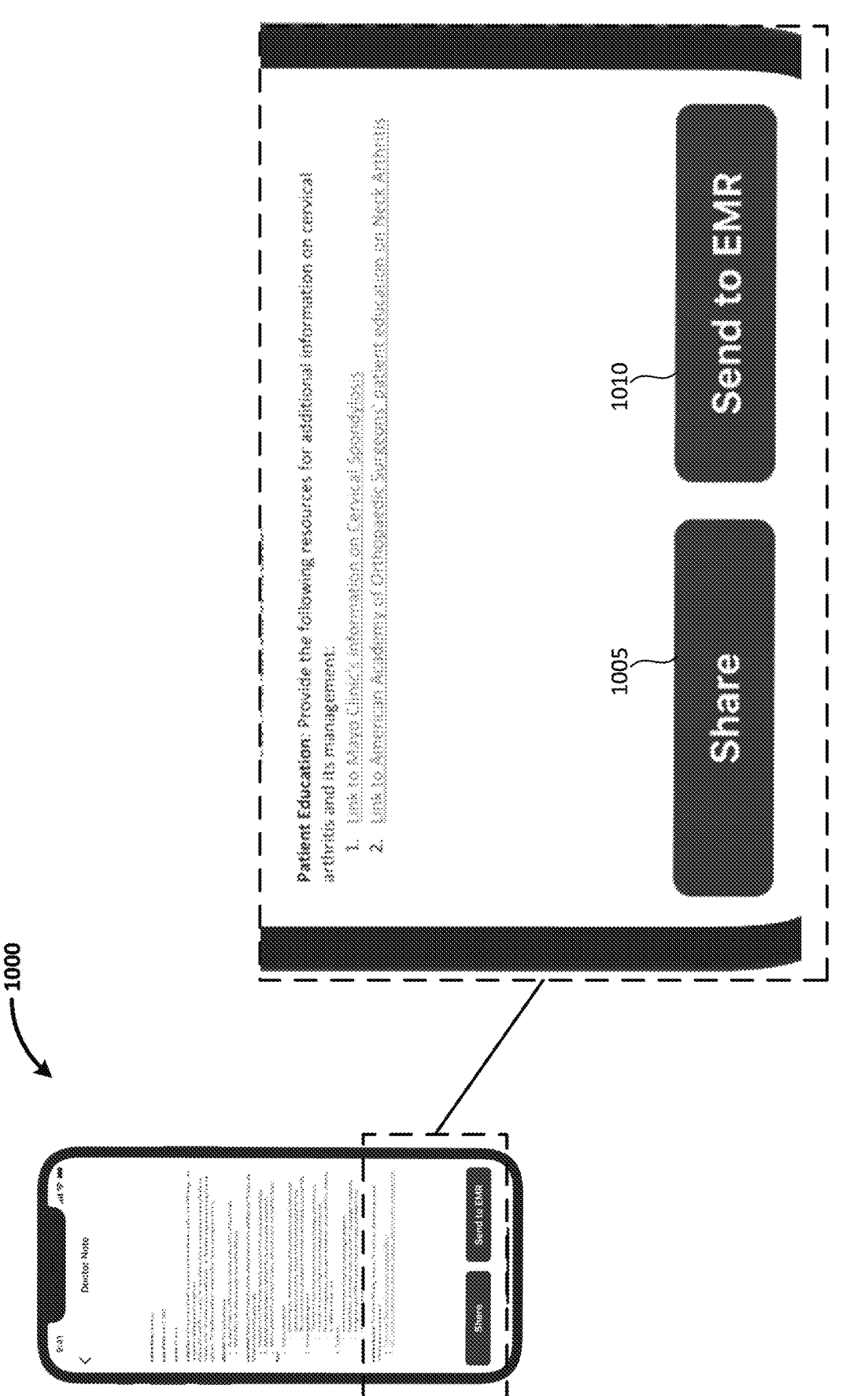

FIG. 10A, FIG. 10B, and FIG. 10C depict an exemplary doctor note 1000 displayed on a user device. In the example, the template is represented as a SOAP note. In some implementations, the exemplary doctor note 1000 may be generated automatically (e.g., by the HIGS 105) based on a detected activity (e.g., one or more follow up events) of a user (e.g., Ava Rose in this example). For example, the doctor note may be displayed when one of the activities displayed in the profile page 920. As shown, a user may select a share button 1005 to share the exemplary doctor note

1000 to a target user. For example, the HCDP 900 may authenticate whether the user has the right to share with the target user. Also, the user may select a send to EMR button 1010 to save the exemplary doctor note 1000 to the EMR 145 associated with the patient.

Figure 11:
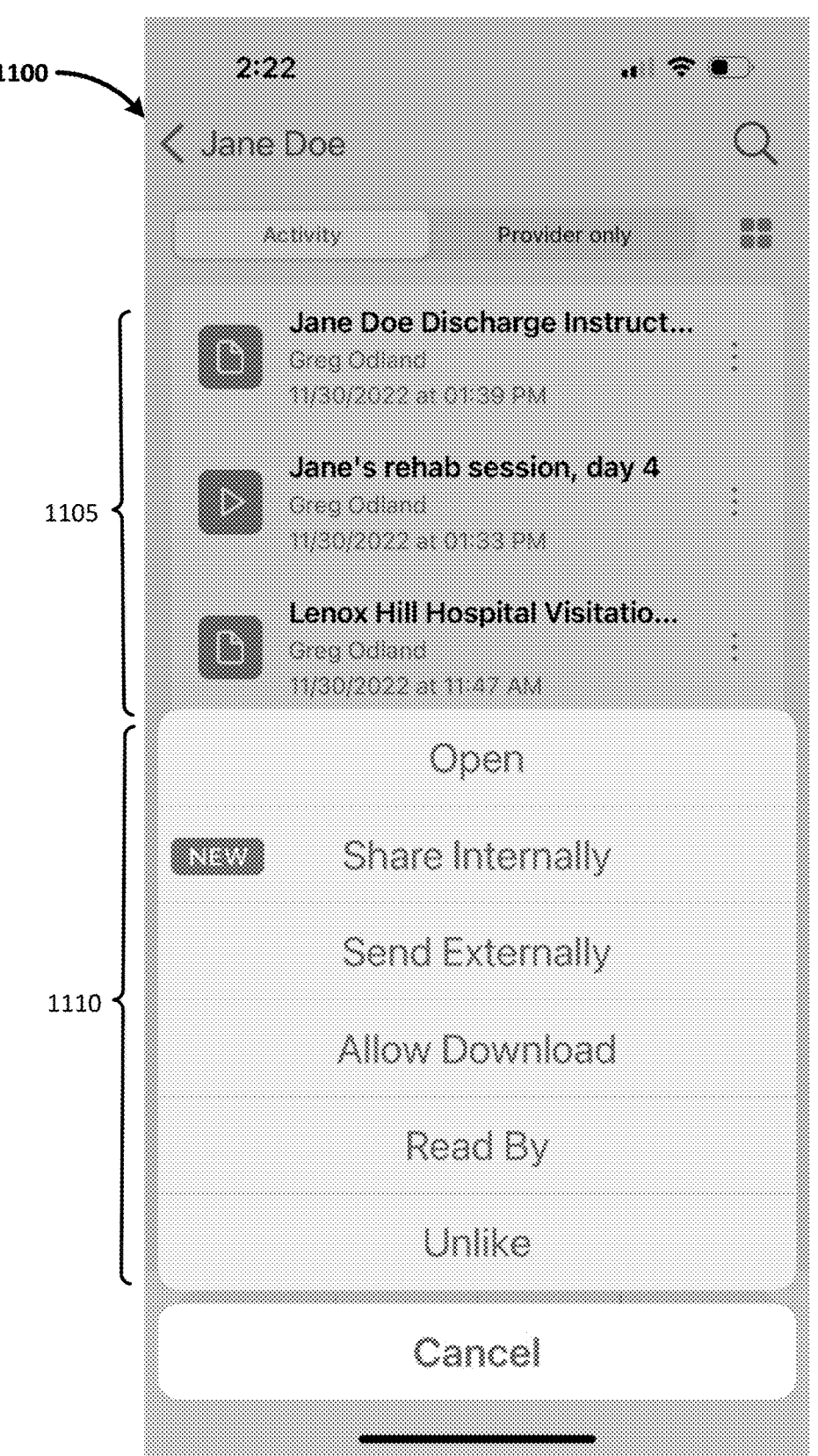
FIG. 11 depicts an exemplary action menu of an exemplary HCDP user interface.

FIG. 11 depicts an exemplary action menu of an exemplary HCDP user interface 1100. In this example, upon selecting a content 1105, an action menu 1110 is displayed.

Figure 12A:
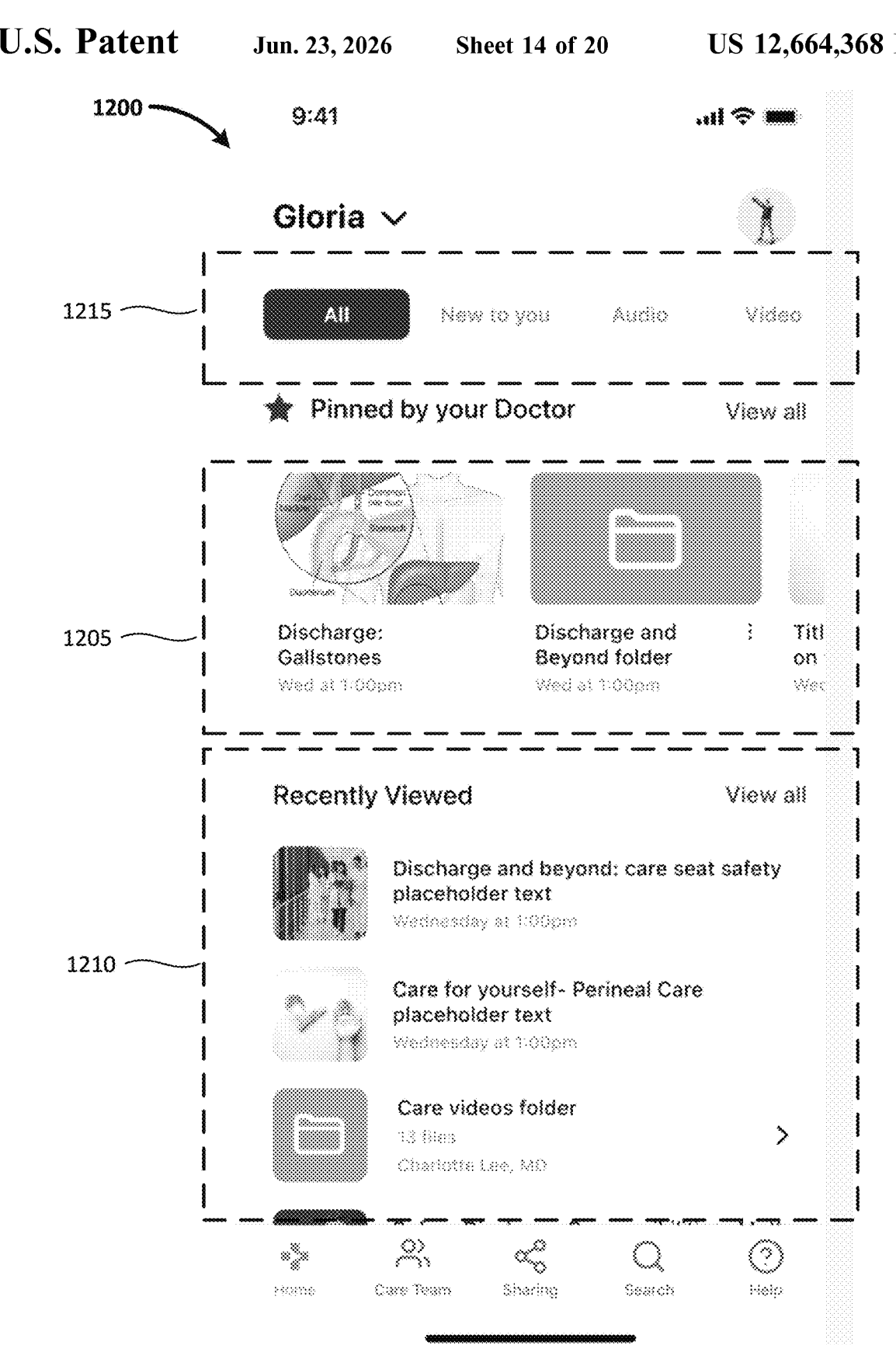
FIG. 12A and FIG. 12B depict an exemplary home page display and content display on an exemplary HCDP user interface.
Figure 12B:
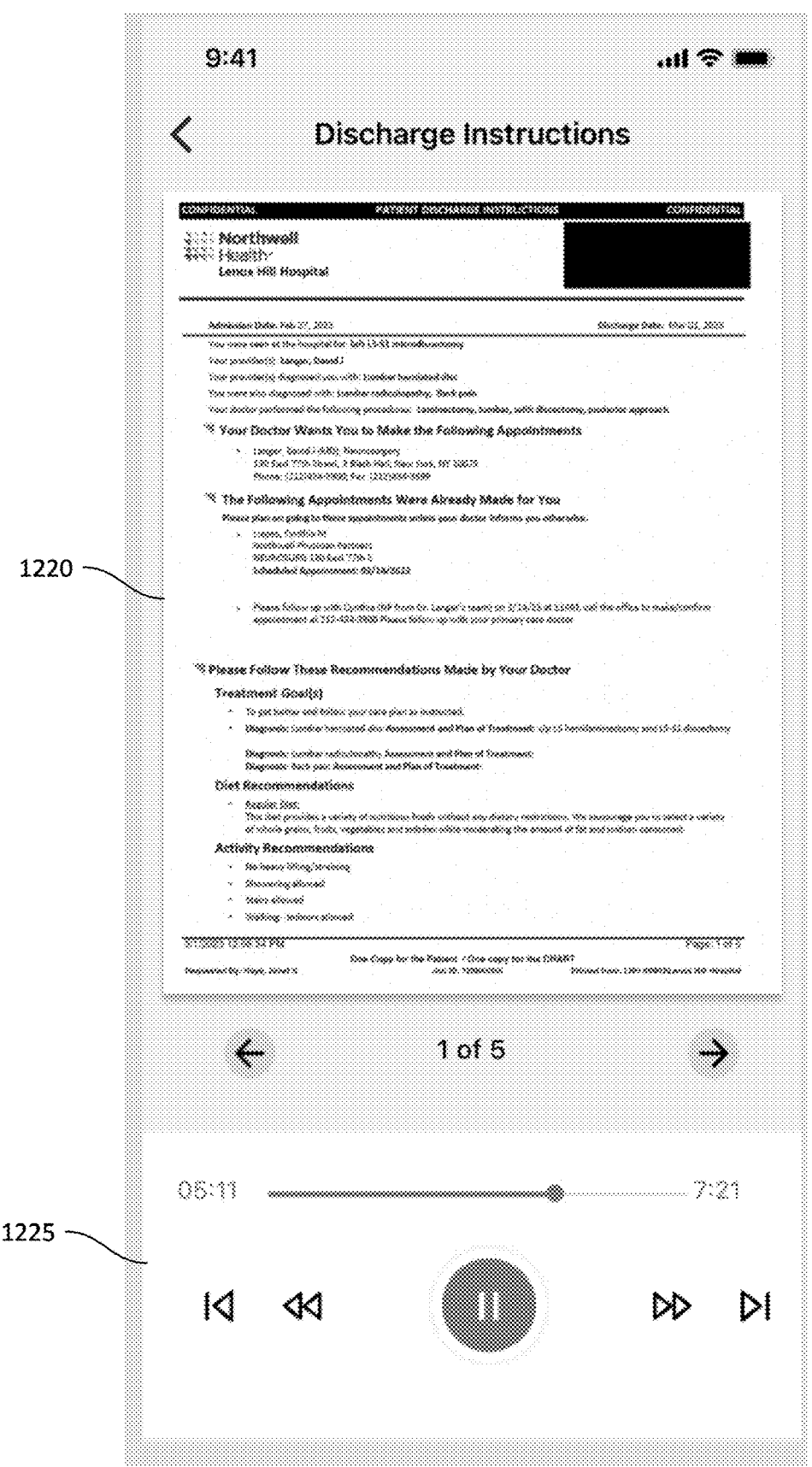

FIG. 12A and FIG. 12B depict an exemplary home page display and content display on an exemplary HCDP user interface. As shown in FIG. 12A, a patient side user interface (PSUI 1200) may include a pinned section 1205 and a recently viewed section 1210. For example, the pinned section 1205 may include content pinned by one or more doctors of the patient (e.g., "Gloria" in this example). The recently viewed section 1210, for example, may include digital content recently viewed by the patient. The PSUI 1200 also includes a content filter 1215. For example, a user may use the content filter 1215 to display all content, new content, audio content, or video content.

As shown in FIG. 12B, the PSUI 1200 displays a selected content 1220. For example, the selected content may be generated when a text note listed in the recently viewed section 1210 is selected. In this example, a voice transcription 1225 of the selected content 1220 is generated. For example, the voice transcription 1225 may be generated by the transcription engine 955. For example, a user may listen to a text note using the voice transcription 1225.

Figure 13:
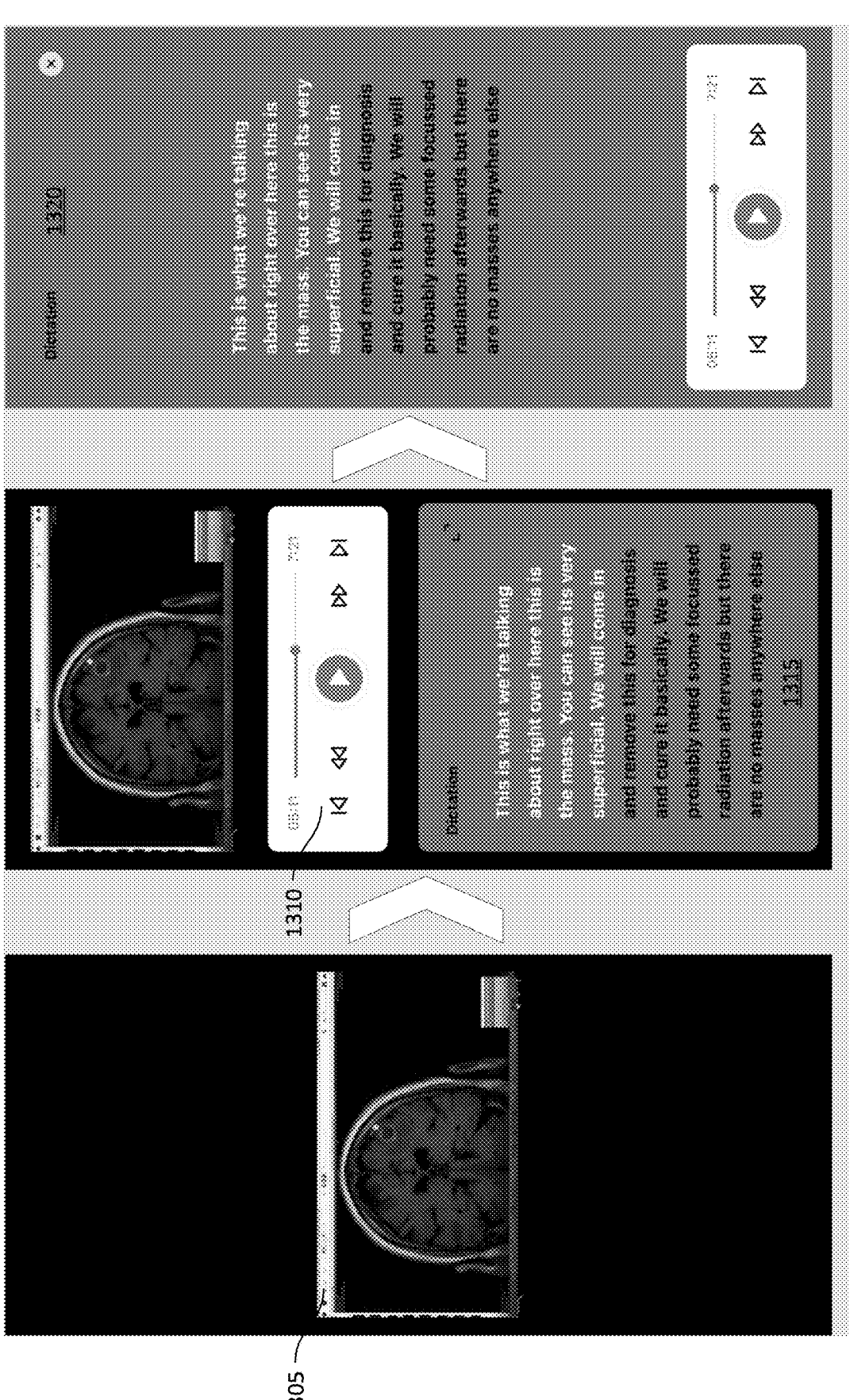
FIG. 13 depicts exemplary video transcription user interfaces.

FIG. 13 depicts exemplary video transcription user interfaces. As shown, a content to be displayed is a video clip 1305. In this example, the video clip 1305 may include a voice explanation 1310 of a radiographic image of a patient. In some implementations, the HCDP 900 may automatically generate a transcription of the explanation into a text format 1315. For example, the patient may expand the text format 1315 into a full screen mode 1320 to advantageously read the text easily.

Figure 14:
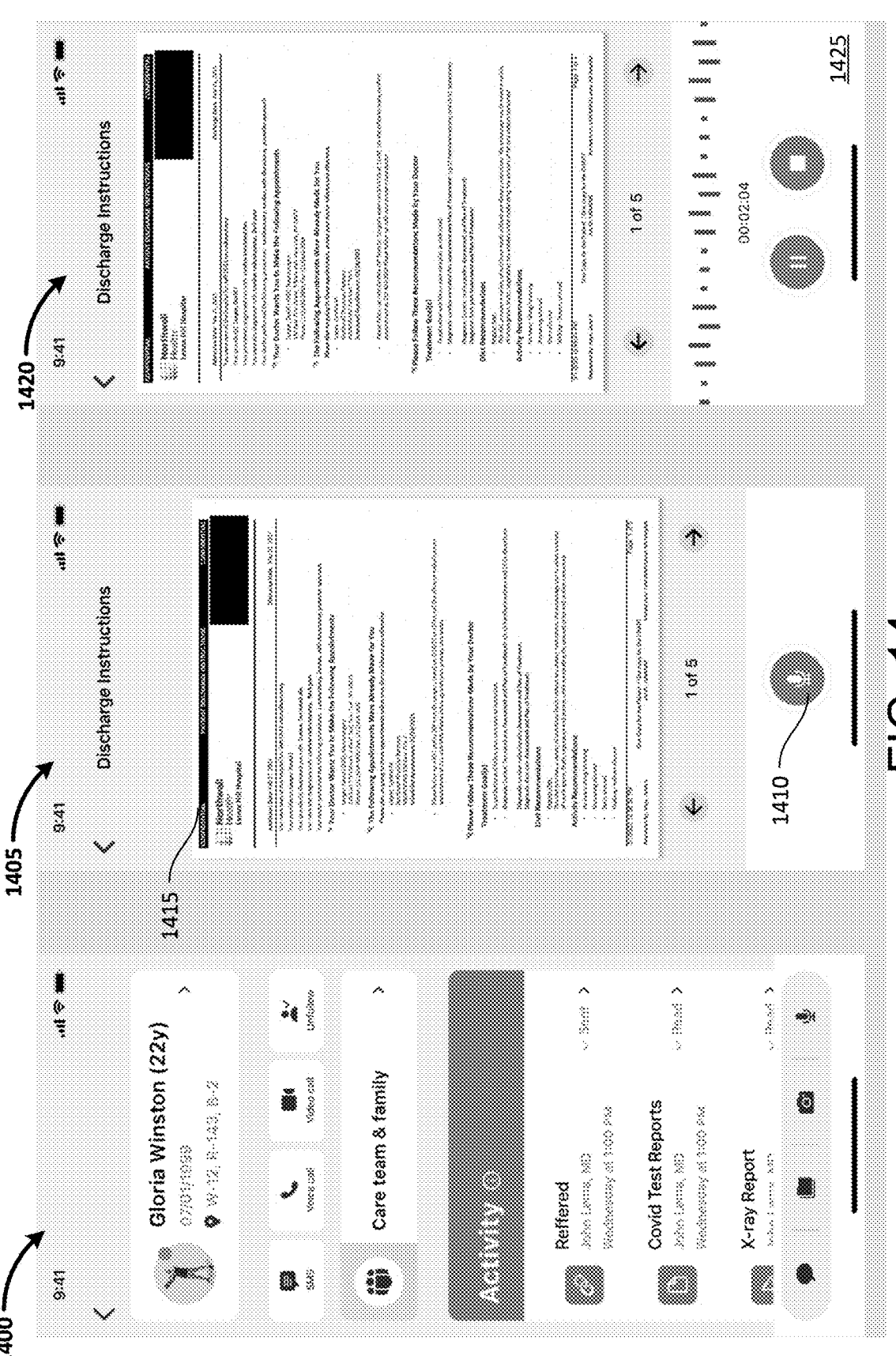
FIG. 14 depicts exemplary care-side user interfaces of an exemplary Health Content Distribution Platform (HCDP) on a user mobile device.

FIG. 14 depicts exemplary care-side user interfaces of an exemplary Health Content Distribution Platform (HCDP) on a user mobile device. As shown, in a user interface 1400, a carer (e.g., a doctor, a caregiver) may view a patient profile page (e.g., upon authentication). In a user interface 1405, the carer may record a voice slip 1410 to explain a document 1415 prepared for the patient. After the explanation is recorded, in this example, a user interface 1420 includes a preview area 1425. For example, the carer may use the preview area 1425 to preview the recorded sound clip.

In some implementations, content creation may be two-way. For example, a patient (e.g., Gloria Winston in the example shown in FIG. 14), a family member of the patient, and/or an outside care provider (e.g., an EMS provider) may also create content in text, image, video, and/or voice to the care provider. As an illustrative example without limitation, the content may include a picture of a wound. For example, the content may include a video of patient therapy. For example, content may include a video of an exercise or gait. For example, the content may include heart data from a wearable. In some examples, the HCDP 900 may digitize received data and content. For example, the HCDP 900 may automatically update the digitized data and content to be displayed on the profile page 920 for access based on access rights of, for example, internal care provider, medical device representatives. For example, the HCDP 900 may also automatically submit the digitized content to the EMR 145.

Figure 15:
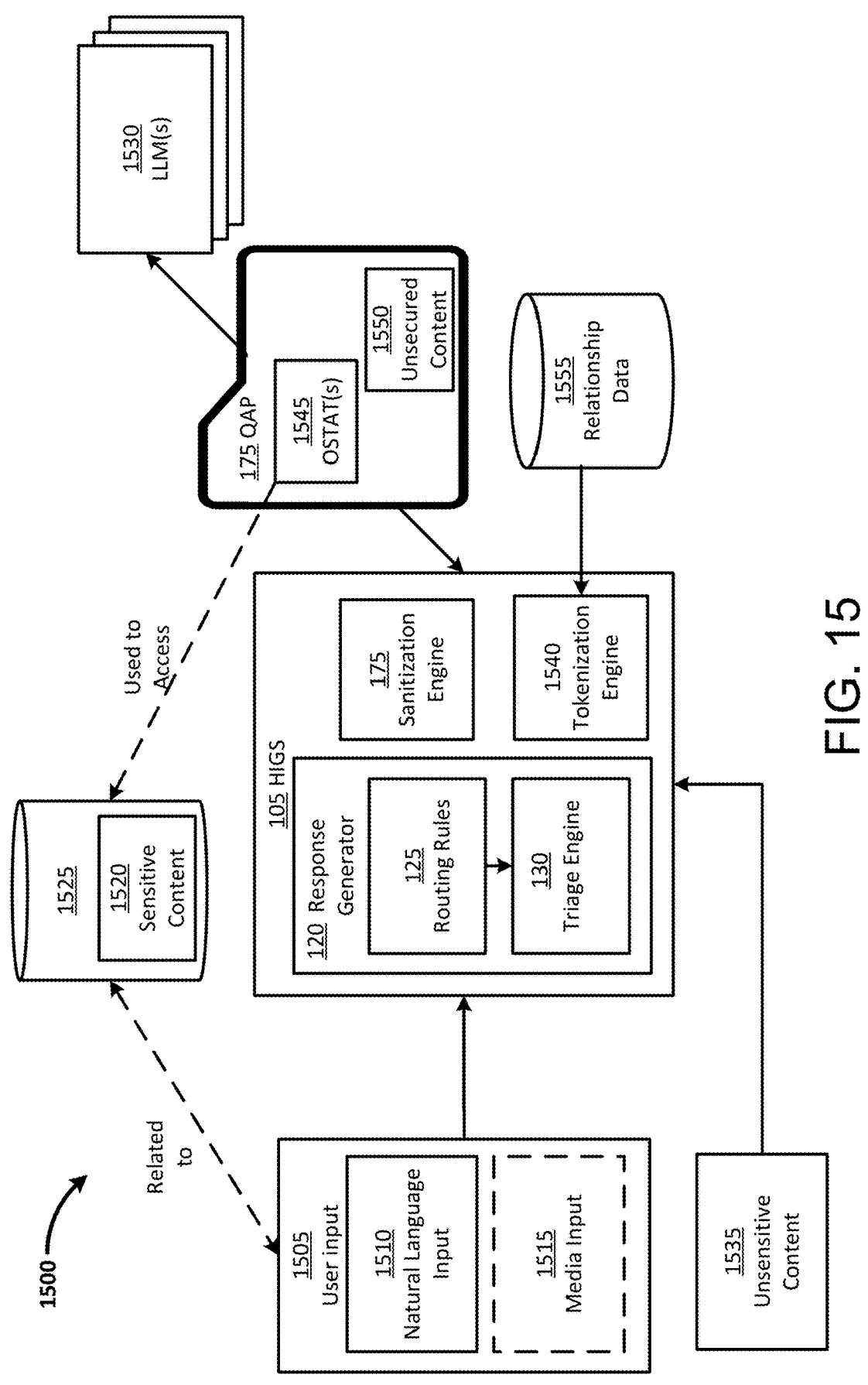
FIG. 15 is a block diagram depicting an exemplary HIGS providing a transient access to one or more secured and/or unsecured LLM.

FIG. 15 is a block diagram depicting an exemplary HIGS providing a transient access to one or more secured and/or unsecured LLM. In an exemplary scenario 1500, the HIGS

105 is configured to receive a user input 1505 from a user device (e.g., the mobile device 111*a*, the mobile device 111*b*, the computing device 116). As shown, the user input 1505 includes a natural language input 1510 and a media input 1515. For example, the media input 1515 may include a natural language prompt (e.g., a query) to be asked at the HIGS 105 (e.g., with respect to a patient).

In some implementations, the media input 1515 may be optional in the user input 1505. For example, the media input 1515 may include a media content associated with the media input 1515. For example, the media input 1515 may include one or more images. For example, the media input 1515 may include a video. For example, the media input 1515 may include a voice. In some examples, a user may transmit the user input 1505 using the media input 1515 independent of the natural language input 1510.

In some implementations, when the HIGS 105 receives the user input 1505, the HIGS 105 may be configured to automatically route and securely transmit artificial intelligence input packages from sensitive data. For example, the user input 1505 may include a voice and/or voice prompt. For example, the user input 1505 may be related to a patient registered in the HIGS 105.

In some implementations, the HIGS 105 may determine various media objects extrinsic to the user input 1505 and associated with the user input 1505. In this example, the user input 1505 may be determined to be related to a sensitive content 1520 and/or an insecurity content 1535. In some examples, the user input 1505 may be related to a sensitive content 1520 (e.g., the PHI) of the patient stored in a sensitive content repository 1525. For example, the sensitive content repository 1525 may include the structured database 140. For example, the sensitive content repository 1525 may include the unstructured database 135. In some implementations, the sensitive content 1520 may include electronic health data (EHD) of the patient. For example, the sensitive content 1520 may include protected and/or sensitive media objects (images, videos, documents, voice clips).

In some implementations, in response to receiving the user input 1505, the response generator 120 may generate a secured large language model (LLM) input array (e.g., the QAP 185 as shown in FIGS. 1 and 15) based on the user input 1505 and the sensitive content 1520. For example, the triage engine 130 may determine, from LLMs 1530 connected to the HIGS 105, at least one selected LLM by applying the routing rules 125 to the user input 1505. For example, the routing rules 125 may include rules considering, for each of the LLMs 1530, a correspondence between the LLM and at least one attribute the user input 1505. For example, the sanitation engine 175 may generate the QAP 185 when the triage engine 130 determines that the LLMs 1530 includes an unsecure LLM (e.g., the public LLM 170) based on at least one attribute of: the user input 1505 and the related media content.

In some implementations, the sanitation engine 175 may be configured to determine, for each of the user input 1505 and each of the media objects associated with the user input 1505 (e.g., the insecurity content 1535 and the sensitive content 1520) individually, a security sensitivity determination.

As shown, the HIGS 105 includes a tokenization engine 1540. For example, the tokenization engine 1540 may be configured to generate an object-specific transient access token (OSTAT) for each of the media objects and the user input that is determined to be security sensitive by the sanitation engine 175.

For example, after receiving the OSTATs generated by the tokenization engine 1540, the sanitation engine 175 may generate the QAP 185. In this example, the QAP 185 includes OSTAT(s) 1545 and unsecured content 1550 (e.g., media objects that may be determined to be not security sensitive). For example, when the LLMs 1530 may receive the QAP 185 and use the OSTAT(s) 1545 to access the sensitive content 1520 for generating a human-readable response to the HIGS 105 (e.g., via corresponding object-specific transient access tokens). For example, each of the OSTAT(s) 1545 may include individual temporary streaming access to the sensitive content 1520 based on one or more relationship determinations. For example, the one or more relationship determination may be stored in a relationship data repository 1555. For example, the one or more relationship determination may include a first predetermined access determination between a user of the user device and the patient. For example, the user may include a carer of the patient. For example, the user may include an insurance company of the patient. For example, the user may include a physician of the patient.

For example, the one or more relationship determination may include a second predetermined access determination between a role of the user and a metadata associated with a corresponding security sensitive media object. For example, the role of the user may include a doctor. For example, the role of the user may include a nurse. For example, the role of the user may include an insurance administrator. For example, the corresponding security sensitive media object may include an insurance claim form. For example, the corresponding security sensitive media object may include an appointment of the patient. For example, the corresponding security sensitive media object may include a prescription.

For example, the one or more relationship determination may include a third predetermined access determination between the user and an originator of the corresponding security sensitive media object. For example, the third access determination may allow a content requestor (the user) in the same enterprise of the content creator to be granted access to the sensitive content 1520.

For example, the triage engine 130 may select one or more of the LLMs 1530 to generate a response to the user input 1505 based on a trained classification model (e.g., the RCM 270) configured to select one or more combinations of LLMs as a function of the user input 1505 and a user profile associated with the user device that transmits the user input (e.g., from the user profile database 260). Various embodiments for generating transient access to secured data are described in detail with reference to PCT Patent Application Serial No. PCT/US22/72888, titled "MULTI-PARTY CONTROLLED TRANSIENT USER CREDENTIALING FOR INTERACTION WITH PATIENT HEALTH DATA," co-authored and filed by Gregory Odland, et al., on Jun. 10, 2022. The entire content of the aforementioned application is incorporated herein by reference.

FIG. 16 is a flowchart illustrating an exemplary tokenized sensitive inquiry routing method. For example, the HIGS 105 may perform a method 1600 as depicted. In this example, the method 1600 begins in step 1605 when a user input including natural language input and data related to health information of a patient is received from a user device. For example, the HIGS 105 may receive the user input 1505 from a user device (e.g., the mobile device 111*a*, the mobile device 111*b*, the computing device 116).

Next, in step 1610, at least one LLM is selected. For example, the triage engine 130 may select one or more LLM from the LLMs 1530. At decision point 1620, it is determined whether to generate a secured LLM input. For example, the sanitation engine 175 may assess if the sensitive content 1520 may include and/or be associated with contains sensitive information (e.g., the sensitive content 1520).

If the secured LLM input is not to be generated, in step 1625, an unsecure LLM input is generated based on the user input and the EHD to the at least one selected LLM, and the method 1600 ends. For example, the triage engine 130 may directly generate the QAP 185 without generating the OSTAT(s) 1545, the user input 1505 is determined to be not sensitive.

In step 1630, if the secured LLM input is to be generated, a desensitization engine is applied to the user input and the media objects. For example, the sanitation engine 175 may be used to process the user input and media objects to remove or replace sensitive data, ensuring the generated input is secure.

In step 1635, for each media object and the user input determined to be security sensitive by the desensitization engine, a corresponding object-specific transient access token is generated. For example, the tokenization engine 1540 may generate unique, temporary tokens each corresponding one of the sensitive content 1520 to allow secure access during processing.

In step 1640, the secured LLM input array is generated based on the user input and the EHD, including the corresponding object-specific transient access tokens and any media objects not determined to be security sensitive, and the method 1600 ends. For example, the triage engine 130 may generate the QAP 185 to the LLMs 1530.

Figure 17:
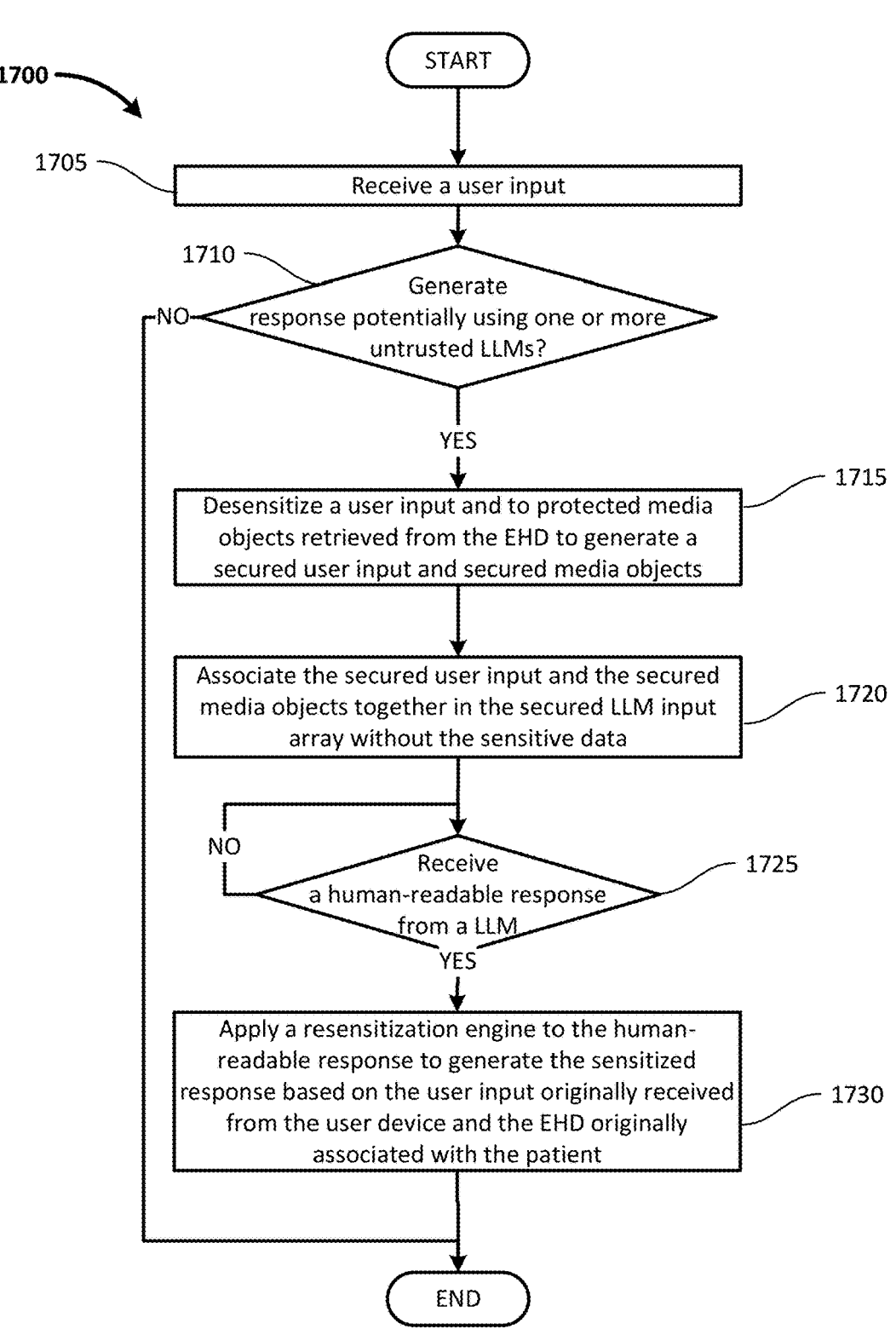
FIG. 17 is a flowchart illustrating an exemplary secured artificial intelligence input packages generation method.

FIG. 17 is a flowchart illustrating an exemplary secured artificial intelligence input packages generation method. For example, a method 1700 may be performed by the HIGS 105 after a user query is received. In this example, the method 1700 begins in step 1705 when a user input is received. For example, the HIGS 105 may receive a query from a user device related to the health information (e.g., EHD) of a patient. For example, the user input and the EHD comprise sensitive data not suitable for sharing with a human-readable responding interaction system comprising an unsecured LLM.

At decision point 1710, it is determined whether to generate a response potentially using one or more untrusted LLMs. For example, the routing engine 240 may determine whether a LLM selected from the LLMs 1530 is a PHI approved LLM 165.

If one or more untrusted LLMs is to be used, the method 1700 ends. If one or more untrusted LLMs is to be used, in step 1715, a desensitization engine is applied to the user input and to protected media objects retrieved from the EHD to generate a secured user input and secured media objects. For example, the sensitive data is at least one of: removed and replaced such that a secured user input and secured media objects are generated. For example, the sanitation engine 175 may remove or replace sensitive data from the natural language input 1510.

In step 1720, the secured user input and the secured media objects are associated together in the secured LLM input array without the sensitive data. For example, when the secured LLM input array is provided to a human-readable responding interaction system (e.g., the LLMs 1530), a human-readable response is generated to the secured LLM input array by at least the unsecured LLM based on the secured media objects. For example, the triage engine 130 may combine the processed inputs into a single array that can be safely shared with the untrusted LLM (e.g., the public LLM 170).

At decision point 1725, it is determined whether a human-readable response has been received from the LLM. For example, the human-readable response is not a direct response to the user input received from the user device. For example, the HIGS 105 may wait for the external LLM to generate and return a response based on the secured input array.

In step 1730, a resensitization engine is applied to the human-readable response to generate the sensitized response based on the user input originally received from the user device and the EHD originally associated with the patient, and the method 1700 ends. For example, the human-readable response from the human-readable responding interaction system is regenerated to comprise at least some of the sensitive data. For example, the sanitation engine 175 may reintroduce the sensitive data to the response to make it relevant and specific to the original query.

Although various embodiments have been described with reference to the figures, other embodiments are possible. For example, the DHC may include sound and images. For example, the images may include MRI images. For example, the DHC may include a Digital Imaging and Communications in Medicine (DICOM).

Although an exemplary system has been described with reference to the figures, other implementations may be deployed in other industrial, scientific, medical, commercial, and/or residential applications.

For example, some embodiments may advantageously store structured data, unstructured data, or a combination thereof. For example, a video and/or audio message received may be transcribed. The transcription, for example, may be inserted into an EMR record (e.g., corresponding to a patient who sent or received the message). In some implementations, the message may include a voice note from a physician and/or other caretakers associated with a patient. The message may be transcribed and inserted, by way of example and not limitation, as a doctor's note in the EMR for the patient's record. Accordingly, various embodiments may advantageously generate structured data from unstructured data.

Computer program products may contain a set of instructions that, when executed by a processor device, cause the processor to perform prescribed functions. These functions may be performed in conjunction with controlled devices in operable communication with the processor. Computer program products, which may include software, may be stored in a data store tangibly embedded on a storage medium, such as an electronic, magnetic, or rotating storage device, and may be fixed or removable (e.g., hard disk, floppy disk, thumb drive, CD, DVD).

Although an example of a system, which may be portable, has been described with reference to the above figures, other implementations may be deployed in other processing applications, such as desktop and networked environments.

Temporary auxiliary energy inputs may be received, for example, from chargeable or single use batteries, which may enable use in portable or remote applications. Some embodiments may operate with other DC voltage sources, such as 9V batteries, for example. Alternating current (AC) inputs, which may be provided, for example from a 50/60 Hz power port, or from a portable electric generator, may be received via a rectifier and appropriate scaling. Provision for AC (e.g., sine wave, square wave, triangular wave) inputs may include a line frequency transformer to provide voltage step-up, voltage step-down, and/or isolation.

Although particular features of an architecture have been described, other features may be incorporated to improve performance. For example, caching (e.g., L1, L2, . . . ) techniques may be used. Random access memory may be included, for example, to provide scratch pad memory and or to load executable code or parameter information stored for use during runtime operations. Other hardware and software may be provided to perform operations, such as network or other communications using one or more protocols, wireless (e.g., infrared) communications, stored operational energy and power supplies (e.g., batteries), switching and/or linear power supply circuits, software maintenance (e.g., self-test, upgrades), and the like. One or more communication interfaces may be provided in support of data storage and related operations.

Some systems may be implemented as a computer system that can be used with various implementations. For example, various implementations may include digital circuitry, analog circuitry, computer hardware, firmware, software, or combinations thereof. Apparatus can be implemented in a computer program product tangibly embodied in an information carrier, e.g., in a machine-readable storage device, for execution by a programmable processor; and methods can be performed by a programmable processor executing a program of instructions to perform functions of various embodiments by operating on input data and generating an output. Various embodiments can be implemented advantageously in one or more computer programs that are executable on a programmable system including at least one programmable processor coupled to receive data and instructions from, and to transmit data and instructions to, a data storage system, at least one input device, and/or at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, which may include a single processor or one of multiple processors of any kind of computer. Generally, a processor will receive instructions and data from a read-only memory or a random-access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including, by way of example, semiconductor memory devices, such as EPROM, EEPROM, and flash memory devices; magnetic disks, such as internal hard disks and removable disks; magneto-optical disks; and CD-ROM and DVD-ROM disks. The processor and the memory can be supplemented by, or incorporated in, ASICs (application-specific integrated circuits).

In some implementations, each system may be programmed with the same or similar information and/or initialized with substantially identical information stored in volatile and/or non-volatile memory. For example, one data interface may be configured to perform auto configuration, auto download, and/or auto update functions when coupled to an appropriate host device, such as a desktop computer or a server.

In various implementations, the system may communicate using suitable communication methods, equipment, and techniques. For example, the system may communicate with compatible devices (e.g., devices capable of transferring data to and/or from the system) using point-to-point communication in which a message is transported directly from the source to the receiver over a dedicated physical link (e.g., fiber optic link, point-to-point wiring, daisy-chain). The components of the system may exchange information by any form or medium of analog or digital data communication, including packet-based messages on a communication network. Examples of communication networks include, e.g., a LAN (local area network), a WAN (wide area network), MAN (metropolitan area network), wireless and/or optical networks, the computers and networks forming the Internet, or some combination thereof. Other implementations may transport messages by broadcasting to all or substantially all devices that are coupled together by a communication network, for example, by using omni-directional radio frequency (RF) signals. Still other implementations may transport messages characterized by high directivity, such as RF signals transmitted using directional (i.e., narrow beam) antennas or infrared signals that may optionally be used with focusing optics. Still other implementations are possible using appropriate interfaces and protocols such as, by way of example and not intended to be limiting, USB 2.0, Firewire, ATA/IDE, RS-232, RS-422, RS-485, 802.11 a/b/g, Wi-Fi, Ethernet, IrDA, FDDI (fiber distributed data interface), token-ring networks, multiplexing techniques based on frequency, time, or code division, or some combination thereof. Some implementations may optionally incorporate features such as error checking and correction (ECC) for data integrity, or security measures, such as encryption (e.g., WEP) and password protection.

In various embodiments, the computer system may include Internet of Things (IoT) devices. IoT devices may include objects embedded with electronics, software, sensors, actuators, and network connectivity which enable these objects to collect and exchange data. IoT devices may be in-use with wired or wireless devices by sending data through an interface to another device. IoT devices may collect useful data and then autonomously flow the data between other devices.

In an illustrative aspect, a system may include a data store. For example, the data store may include a program of instructions. For example, the system may include a processor operably coupled to the data store. For example, when the processor executes the program of instructions, the processor causes operations to be performed to automatically generate secured artificial intelligence input packages from sensitive data input, the operations may include, in response to a user input received from a user device including a natural language input and related to electronic health data (EHD) of a patient, generate a secured large language model (LLM) input array based on the user input and the EHD. For example, the user input and the EHD may include sensitive data not suitable for sharing with a human-readable responding interaction system may include an unsecured LLM.

For example, generating the secured LLM input array may include, when a routing engine determines that the human-readable responding interaction system may include an unsecure LLM based on at least one attribute of: the user input and the EHD, apply a desensitization engine to the user input and to protected media objects retrieved from the EHD based on the user input. For example, the sensitive data may be at least one of: removed and replaced. For example, a secured user input and secured media objects may be generated.

For example, generating the secured LLM input array may include associate the secured user input and the secured media objects together in the secured LLM input array without the sensitive data. For example, when the secured LLM input array may be provided to the human-readable responding interaction system, a human-readable response may be generated to the secured LLM input array by at least the unsecured LLM based on the secured media objects.

For example, generating the secured LLM input array may include, in response to receiving the human-readable response to the secured user input from the human-readable responding interaction system. For example, the human-readable response may be not a direct response to the user input received from the user device. For example, the operations may include transform the human-readable response into a sensitized response to the user input by performing resensitization operations.

For example, the resensitization operations may include apply a resensitization engine to the human-readable response to generate the sensitized response based on the user input originally received from the user device and the EHD originally associated with the patient. For example, the human-readable response from the human-readable responding interaction system may be regenerated to include at least some of the sensitive data. For example, the sensitized response may be the direct response to the user input originally received from the user device.

For example, the system may include none of, any of, or some combinations of the following features:

For example, the routing engine may determine one or more LLMs to be selected to generate an response to the user input originally received from the user device based on a trained classification model configured to select one or more combinations of LLMs to be used as a function of the user input and a user profile associated with the user device that transmits the user input.

For example, the desensitization engine may include a trusted LLM configured to generate the secured LLM input array by transforming the user input and the EHD into the secured LLM input array.

For example, the resensitization engine may include a trusted LLM configured to generate the sensitized response by transforming the response from the human-readable responding interaction system into the sensitized response based on the user input and the EHD of the patient.

For example, generating the secured LLM input array further may include determine, from a plurality of LLMs, at least one selected LLM by applying a routing engine to the user input. For example, the at least one selected LLM may be determined based on a correspondence between the at least one selected LLM and at least one attribute of at least one of: the original user input, and media objects retrieved from the EHD based on the user input. For example, the media objects may include the protected media objects. For example, when apply a desensitization engine to the user input and to the media objects, determine, for each of the user input and each of the media objects individually, a security sensitivity determination. For example, for each of the media objects and the user input that may be determined to be security sensitive by the desensitization engine, generate, by a tokenization engine, an object-specific transient access token. For example, a plurality of object-specific transient access tokens may be generated. For example, generating the secured LLM input array further may include generate, by the desensitization engine, the secured LLM input array may include the plurality of object-specific transient access tokens and any media objects not determined to be security sensitive. For example, when the secured LLM input array may be provided to the human-readable responding interaction system, the media objects determined to be security sensitive may be transiently available to the human-readable responding interaction system for generating the human-readable response via corresponding object-specific transient access tokens.

For example, each of the plurality of object-specific transient access tokens may include individual temporary streaming access to the security sensitive media objects based on one or more relationship determinations. For example, the one or more relationship determinations may include a first predetermined access determination between a user of the user device and the patient, a second predetermined access determination between a role of the user and a metadata of associated with a corresponding security sensitive media object, and a third predetermined access determination between an originator of the corresponding security sensitive media object.

In an illustrative aspect, a computer-implemented method performed by at least one processor to automatically generate secured artificial intelligence input packages from sensitive data input, the method may include, in response to a user input received from a user device may include a natural language input and related to electronic health data (EHD) of a patient, generate a secured large language model (LLM) input array based on the user input and the EHD. For example, the user input and the EHD may include sensitive data not suitable for sharing with a human-readable responding interaction system may include an unsecured LLM.

For example, generating the secured LLM input array may include apply a desensitization engine to the user input and to protected media objects retrieved from the EHD based on the user input. For example, the sensitive data may be at least one of: removed and replaced. For example, a secured user input and secured media objects may be generated.

For example, generating the secured LLM input array may include associate the secured user input and the secured media objects together in the secured LLM input array without the sensitive data. For example, when the secured LLM input array may be provided to the human-readable responding interaction system, a human-readable response may be generated to the secured LLM input array by at least the unsecured LLM based on the secured media objects.

For example, generating the secured LLM input array may include, in response to receiving the human-readable response to the secured user input from the human-readable responding interaction system. For example, the human-readable response may be not a direct response to the user input received from the user device, transform the human-readable response into a sensitized response to the user input by performing resensitization operations.

For example, the resensitization operations may include apply a resensitization engine to the human-readable response to generate the sensitized response based on the user input originally received from the user device and the EHD originally associated with the patient. For example, the human-readable response from the human-readable responding interaction system may be regenerated to may include at least some of the sensitive data. For example, the sensitized response may be the direct response to the user input originally received from the user device.

For example, the computer-implemented method may include none of, any of, or some combinations of the following features:

For example, the secured LLM input array may be generated by the desensitization engine when a routing engine determines that the human-readable responding interaction system may include an unsecure LLM based on at least one attribute of: the user input and the EHD.

For example, the routing engine determines one or more LLMs to be selected to generate a response to the user input originally received from the user device based on a trained classification model configured to select one or more combinations of LLMs to be used as a function of the user input and a user profile associated with the user device that transmits the user input.

For example, the desensitization engine may include a trusted LLM configured to generate the secured LLM input array by transforming the user input and the EHD into the secured LLM input array.

For example, the resensitization engine may include a trusted LLM configured to generate the sensitized response by transforming the response from the human-readable responding interaction system into the sensitized response based on the user input and the EHD of the patient.

For example, generating the secured LLM input array further may include determine, from a plurality of LLMs, at least one selected LLM by applying a routing engine to the user input. For example, the at least one selected LLM may be determined based on a correspondence between the at least one selected LLM and at least one attribute of at least one of: the original user input, and media objects retrieved from the EHD based on the user input. For example, the media objects may include the protected media objects. For example, when apply a desensitization engine to the user input and to the media objects, determine, for each of the user input and each of the media objects individually, a security sensitivity determination. For example, for each of the media objects and the user input that may be determined to be security sensitive by the desensitization engine, generate, by a tokenization engine, an object-specific transient access token. For example, a plurality of object-specific transient access tokens may be generated. For example, generating the secured LLM input array further may include generate, by the desensitization engine, the secured LLM input array may include the plurality of object-specific transient access tokens and any media objects not determined to be security sensitive. For example, when the secured LLM input array may be provided to the human-readable responding interaction system, the media objects determined to be security sensitive may be transiently available to the human-readable responding interaction system for generating the human-readable response via corresponding object-specific transient access tokens.

For example, each of the plurality of object-specific transient access tokens may include individual temporary streaming access to the security sensitive media objects based on one or more relationship determinations. For example, the one or more relationship determinations may include a first predetermined access determination between a user of the user device and the patient, a second predetermined access determination between a role of the user and a metadata of associated with a corresponding security sensitive media object, and a third predetermined access determination between an originator of the corresponding security sensitive media object.

In an illustrative aspect, a computer program product may include a program of instructions tangibly embodied on a non-transitory computer readable medium. For example, when the instructions may be executed on a processor, the processor causes data transformation and transmission operations to be performed to automatically route and securely transmit artificial intelligence input packages from sensitive data, the operations may include, in response to a user input received from a user device a may include a natural language input and related to electronic health data (EHD) of a patient, generate a secured large language model (LLM) input array based on the user input and the EHD.

For example, generating the secured LLM input array may include determine, from a plurality of LLMs, at least one selected LLM by applying a routing engine to the user input. For example, the at least one selected LLM may be determined based on a correspondence between the at least one selected LLM and at least one attribute of at least one of: the user input received from the user device, and media objects retrieved from the EHD based on the user input. For example, the media objects may include protected media objects.

For example, generating the secured LLM input array may include apply a desensitization engine to the user input and to the media objects. For example, a security sensitivity determination may be individually made for each of the user input and each of the media objects.

For example, generating the secured LLM input array may include, for each of the media objects and the user input that may be determined to be security sensitive by the desensitization engine, generate, by a tokenization engine, an object-specific transient access token. For example, a plurality of object-specific transient access tokens may be generated.

For example, generating the secured LLM input array may include generate, by the desensitization engine, the secured LLM input array may include the plurality of object-specific transient access tokens and any media objects not determined to be security sensitive. For example, when the secured LLM input array may be provided to the at least one selected LLM, the media objects determined to be security sensitive may be transiently available to the at least one selected LLM for generating the human-readable response via corresponding object-specific transient access tokens.

For example, the computer program product may include none of, any of, or a combination of the following features:

For example, each of the plurality of object-specific transient access tokens may include individual temporary streaming access to the security sensitive media objects based on one or more relationship determinations. For example, the one or more relationship determination may include a first predetermined access determination between a user of the user device and the patient, a second predetermined access determination between a role of the user and a metadata of associated with a corresponding security sensitive media object, a third predetermined access determination between an originator of the corresponding security sensitive media object.

For example, the secured LLM input array may be generated by the desensitization engine when a routing engine determines that the at least one selected LLM may include an unsecure LLM based on at least one attribute of: the user input and the EHD.

For example, the routing engine determines the at least one selected LLM to generate a response to the user input received from the user device based on a trained classification model configured to select one or more combinations of LLMs to be used as a function of the user input and a user profile associated with the user device that transmits the user input.

For example, the user input and the EHD may include sensitive data not suitable for sharing with a human-readable responding interaction system may include an unsecured LLM. For example, apply a desensitization engine to the user input and to the protected media objects may include at least one of: removed and replaced the sensitive data. For example, a secured user input and secured media objects may be generated. For example, generate the secured LLM input array may include associate the secured user input and the secured media objects together in the secured LLM input array without the sensitive data. For example, when the secured LLM input array may be provided to the human-readable responding interaction system, a human-readable response may be generated to the secured LLM input array by at least the unsecured LLM based on the secured media objects. For example, in response to receiving the human-readable response to the secured user input from the human-readable responding interaction system (e.g., the human-readable response may be not a direct response to the user input received from the user device), transform the human-readable response into a sensitized response to the user input by performing resensitization operations may include apply a resensitization engine to the human-readable response to generate the sensitized response based on the user input originally received from the user device and the EHD originally associated with the patient. For example, the human-readable response from the human-readable responding interaction system may be regenerated to may include at least some of the sensitive data. For example, the sensitized response may be the direct response to the user input originally received from the user device.

For example, the desensitization engine may include a trusted LLM configured to generate the secured LLM input array by transforming the user input and the EHD into the secured LLM input array.

For example, the resensitization engine may include a trusted LLM configured to generate the sensitized response by transforming the response from the human-readable responding interaction system into the sensitized response based on the user input and the EHD of the patient.

For example, the system may include any of the features included in the computer-implemented method. For example, the system may include any of the features included in the computer program product. For example, the computer-implemented method may include any of the features included in the computer program product. For example, the computer-implemented method may include any of the features included in the system. For example, the computer program product may include any of the features included in the system. For example, the computer program product may include any of the features included in the computer-implemented method.

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

What is claimed is:

1. A system comprising:
a data store comprising a program of instructions; and,
a processor operably coupled to the data store such that, when the processor executes the program of instructions, the processor causes operations to be performed to automatically generate secured artificial intelligence input packages from sensitive data input, the operations comprising:
  in response to a user input received from a user device comprising a natural language input and related to electronic health data (EHD) of a patient, generate a secured large language model (LLM) input array based on the user input and the EHD, wherein the user input and the EHD comprise sensitive data not suitable for sharing with a human-readable responding interaction system comprising an unsecured LLM, wherein generating the secured LLM input array comprises:
    when a routing engine determines that the human-readable responding interaction system comprises an unsecure LLM based on at least one attribute of: the user input and the EHD, apply a desensitization engine to the user input and to protected media objects retrieved from the EHD based on the user input such that the sensitive data is at least one of: removed and replaced such that a secured user input and secured media objects are generated; and,
    associate the secured user input and the secured media objects together in the secured LLM input array without the sensitive data such that, when the secured LLM input array is provided to the human-readable responding interaction system, a human-readable response is generated to the secured LLM input array by at least the unsecured LLM based on the secured media objects; and,
  in response to receiving the human-readable response to the secured user input from the human-readable responding interaction system, wherein the human-readable response is not a direct response to the user input received from the user device, transform the human-readable response into a sensitized response to the user input by performing resensitization operations comprising:
    apply a resensitization engine to the human-readable response to generate the sensitized response based on the user input originally received from the user device and the EHD originally associated with the patient, wherein the human-readable response from the human-readable responding interaction system is regenerated to comprise at least some of the sensitive data, such that the sensitized response is the direct response to the user input originally received from the user device.

2. The system of claim 1, wherein generating the secured LLM input array further comprises:

determine, from a plurality of LLMs, at least one selected LLM by applying the routing engine to the user input such that the at least one selected LLM is determined based on a correspondence between the at least one selected LLM and at least one attribute of at least one of: the user input originally received, and media objects retrieved from the EHD based on the user input, wherein the media objects comprises the protected media objects;

when apply the desensitization engine to the user input and to the media objects, determine, for each of the user input and each of the media objects individually, a security sensitivity determination;

for each of the media objects and the user input that is determined to be security sensitive by the desensitization engine, generate, by a tokenization engine, an object-specific transient access token such that a plurality of object-specific transient access tokens are generated; and, generate, by the desensitization engine, the secured LLM input array comprising the plurality of object-specific transient access tokens and any media objects not determined to be security sensitive, such that, when the secured LLM input array is provided to the human-readable responding interaction system, the media objects determined to be security sensitive are transiently available to the human-readable responding interaction system for generating the human-readable response via corresponding object-specific transient access tokens.

3. The system of claim 2, wherein each of the plurality of object-specific transient access tokens comprises individual temporary streaming access to the security sensitive media objects based on one or more relationship determinations, wherein the one or more relationship determinations comprise:

a first predetermined access determination between a user of the user device and the patient;

a second predetermined access determination between a role of the user and a metadata of associated with a corresponding security sensitive media object; and, a third predetermined access determination between the user and an originator of the corresponding security sensitive media object.

4. The system of claim 1, wherein the routing engine determines one or more LLMs to be selected to generate a response to the user input originally received from the user device based on a trained classification model configured to select one or more combinations of LLMs to be used as a function of the user input and a user profile associated with the user device that transmits the user input.

5. The system of claim 1, wherein the desensitization engine comprises a trusted LLM configured to generate the secured LLM input array by transforming the user input and the EHD into the secured LLM input array.

6. The system of claim 1, wherein the resensitization engine comprises a trusted LLM configured to generate the sensitized response by transforming the response from the human-readable responding interaction system into the sensitized response based on the user input and the EHD of the patient.

7. A computer-implemented method performed by at least one processor to automatically generate secured artificial intelligence input packages from sensitive data input, the method comprising:

in response to a user input received from a user device comprising a natural language input and related to electronic health data (EHD) of a patient, generate a secured large language model (LLM) input array based on the user input and the EHD, wherein the user input and the EHD comprise sensitive data not suitable for sharing with a human-readable responding interaction system comprising an unsecured LLM, wherein generating the secured LLM input array comprises:

apply a desensitization engine to the user input and to protected media objects retrieved from the EHD based on the user input such that the sensitive data is at least one of: removed and replaced such that a secured user input and secured media objects are generated; and, associate the secured user input and the secured media objects together in the secured LLM input array without the sensitive data such that, when the secured LLM input array is provided to the human-readable responding interaction system, a human-readable response is generated to the secured LLM input array by at least the unsecured LLM based on the secured media objects; and, in response to receiving the human-readable response to the secured user input from the human-readable responding interaction system, wherein the human-readable response is not a direct response to the user input received from the user device, transform the human-readable response into a sensitized response to the user input by performing resensitization operations comprising:

apply a resensitization engine to the human-readable response to generate the sensitized response based on the user input originally received from the user device and the EHD originally associated with the patient, wherein the human-readable response from the human-readable responding interaction system is regenerated to comprise at least some of the sensitive data, such that the sensitized response is the direct response to the user input originally received from the user device.

8. The computer-implemented method of claim 7, wherein the secured LLM input array is generated by the desensitization engine when a routing engine determines that the human-readable responding interaction system comprises an unsecure LLM based on at least one attribute of: the user input and the EHD.

9. The computer-implemented method of claim 8, wherein the routing engine determines one or more LLMs to be selected to generate a response to the user input originally received from the user device based on a trained classification model configured to select one or more combinations of LLMs to be used as a function of the user input and a user profile associated with the user device that transmits the user input.

10. The computer-implemented method of claim 7, wherein generating the secured LLM input array further comprises:

determine, from a plurality of LLMs, at least one selected LLM by applying a routing engine to the user input such that the at least one selected LLM is determined based on a correspondence between the at least one selected LLM and at least one attribute of at least one of: the user input originally received, and media objects retrieved from the EHD based on the user input, wherein the media objects comprises the protected media objects;

when apply the desensitization engine to the user input and to the media objects, determine, for each of the user input and each of the media objects individually, a security sensitivity determination;

for each of the media objects and the user input that is determined to be security sensitive by the desensitization engine, generate, by a tokenization engine, an object-specific transient access token such that a plurality of object-specific transient access tokens are generated; and, generate, by the desensitization engine, the secured LLM input array comprising the plurality of object-specific transient access tokens and any media objects not determined to be security sensitive, such that, when the secured LLM input array is provided to the human-readable responding interaction system, the media objects determined to be security sensitive are transiently available to the human-readable responding interaction system for generating the human-readable response via corresponding object-specific transient access tokens.

11. The computer-implemented method of claim 10, wherein each of the plurality of object-specific transient access tokens comprises individual temporary streaming access to the security sensitive media objects based on one or more relationship determinations, wherein the one or more relationship determinations comprise:

a first predetermined access determination between a user of the user device and the patient;

a second predetermined access determination between a role of the user and a metadata of associated with a corresponding security sensitive media object; and, a third predetermined access determination between the user and an originator of the corresponding security sensitive media object.

12. The computer-implemented method of claim 7, wherein the desensitization engine comprises a trusted LLM configured to generate the secured LLM input array by transforming the user input and the EHD into the secured LLM input array.

13. The computer-implemented method of claim 7, wherein the resensitization engine comprises a trusted LLM configured to generate the sensitized response by transforming the response from the human-readable responding interaction system into the sensitized response based on the user input and the EHD of the patient.

14. A computer program product comprising a program of instructions tangibly embodied on a non-transitory computer readable medium wherein, when the instructions are executed on a processor, the processor causes data transformation and transmission operations to be performed to automatically route and securely transmit artificial intelligence input packages from sensitive data, the operations comprising:

in response to a user input received from a user device comprising a natural language input and related to electronic health data (EHD) of a patient, generate a secured large language model (LLM) input array based on the user input and the EHD, wherein generating the secured LLM input array comprises:

determine, from a plurality of LLMs, at least one selected LLM by applying a routing engine to the user input such that the at least one selected LLM is determined based on a correspondence between the at least one selected LLM and at least one attribute of at least one of: the user input received from the user device, and media objects retrieved from the EHD based on the user input, wherein the media objects comprises protected media objects;

apply a desensitization engine to the user input and to the media objects such that a security sensitivity determination is individually made for each of the user input and each of the media objects;

for each of the media objects and the user input that is determined to be security sensitive by the desensitization engine, generate, by a tokenization engine, an object-specific transient access token such that a plurality of object-specific transient access tokens are generated; and, generate, by the desensitization engine, the secured LLM input array comprising the plurality of object-specific transient access tokens and any media objects not determined to be security sensitive, such that, when the secured LLM input array is provided to the at least one selected LLM, the media objects determined to be security sensitive are transiently available to the at least one selected LLM for generating a human-readable response via corresponding object-specific transient access tokens.

15. The computer program product of claim 14, wherein the secured LLM input array is generated by the desensitization engine when the routing engine determines that the at least one selected LLM comprises an unsecure LLM based on at least one attribute of: the user input and the EHD.

16. The computer program product of claim 15, wherein the routing engine determines the at least one selected LLM to generate a response to the user input received from the user device based on a trained classification model configured to select one or more combinations of LLMs to be used as a function of the user input and a user profile associated with the user device that transmits the user input.

17. The computer program product of claim 14, wherein the user input and the EHD comprise sensitive data not suitable for sharing with a human-readable responding interaction system comprising an unsecured LLM, and wherein:

apply the desensitization engine to the user input and to the protected media objects comprises at least one of: removed and replaced the sensitive data such that a secured user input and secured media objects are generated;

generate the secured LLM input array comprises associate the secured user input and the secured media objects together in the secured LLM input array without the sensitive data such that, when the secured LLM input array is provided to the human-readable responding interaction system, a human-readable response is generated to the secured LLM input array by at least the unsecured LLM based on the secured media objects; and, in response to receiving the human-readable response to the secured user input from the human-readable responding interaction system, wherein the human-readable response is not a direct response to the user input received from the user device, transform the human-readable response into a sensitized response to the user input by performing resensitization operations comprising:

apply a resensitization engine to the human-readable response to generate the sensitized response based on the user input originally received from the user device and the EHD originally associated with the patient, wherein the human-readable response from the human-readable responding interaction system is regenerated to comprise at least some of the sensitive data, such that the sensitized response is the direct response to the user input originally received from the user device.

18. The computer program product of claim 17, wherein the desensitization engine comprises a trusted LLM configured to generate the secured LLM input array by transforming the user input and the EHD into the secured LLM input array.

19. The computer program product of claim 17, wherein the resensitization engine comprises a trusted LLM configured to generate the sensitized response by transforming the response from the human-readable responding interaction system into the sensitized response based on the user input and the EHD of the patient.

20. The computer program product of claim 14, wherein each of the plurality of object-specific transient access tokens comprises individual temporary streaming access to the security sensitive media objects based on one or more relationship determinations, wherein the one or more relationship determination comprises:

a first predetermined access determination between a user of the user device and the patient;

a second predetermined access determination between a role of the user and a metadata of associated with a corresponding security sensitive media object; and, a third predetermined access determination between the user and an originator of the corresponding security sensitive media object.

* * * * *